United States Patent [19]
Le et al.

[11] Patent Number: 6,132,968
[45] Date of Patent: Oct. 17, 2000

[54] METHODS FOR QUANTITATING LOW LEVEL MODIFICATIONS OF NUCLEOTIDE SEQUENCES

[75] Inventors: Xiao-Chun Le; Michael Weinfeld; James Z. Xing, all of Edmonton, Canada

[73] Assignee: University of Alberta, Edmonton, Canada

[21] Appl. No.: 09/078,347

[22] Filed: May 13, 1998

[51] Int. Cl.[7] ............................. C12Q 1/68; G01N 33/53
[52] U.S. Cl. .................................. 435/6; 435/7.1
[58] Field of Search ........................ 435/6, 7.1; 436/501, 436/538, 94

[56] References Cited

U.S. PATENT DOCUMENTS

| | | | |
|---|---|---|---|
| 4,675,300 | 6/1987 | Zare et al. | 204/452 |
| 4,794,074 | 12/1988 | Harris | 435/6 |
| 5,114,551 | 5/1992 | Hjerten et al. | 204/452 |
| 5,556,750 | 9/1996 | Modrich et al. | 435/6 |

OTHER PUBLICATIONS

Randerath et al. (1981) "$^{32}$P–Labeling test for DNA damage," Proc. Natl. Acad. Sci. USA 78P:6126:6129.

Gupta et al. (1996) in *Technologies for Detection of DNA Damage and Mutations*, G.P. Pfeifer (ed.) Plenum, New York, pp. 45–61.

Dizdaroglu (1993) "Quantitative determination of oxidative base damage in DNA by stable isotope–dilution mass spectrometry," FEBS 315:1–6.

Naritsin and Markey (1996) "Assessment of DNA Oxidative Damage by Quantification of Thymidine Glycol Residues Using Gas Chromatography/Electron Capture Negative Ionization Mass Spectrometry," Anal. Biochem. 241:35–41.

Wagner et al. (1992) "Endogenous oxidative damage of deoxycytidine in DNA," Proc. Natl. Acad. Sci. 78:3380–3384.

Leadon and Hanawlat (1983) "Monoclonal antibody to DNA containing thymine glycol," Mutat. Res. 112:191–200.

Cooper et al. (1997) "Defective Transcription–Coupled Repair of Oxidative Base Damage in Cockayne Syndrome Patients from XP Group G," Science 275:990–993.

Melamede et al. (1996) in *Technologies for Detection of DNA Damage and Mutations*, G.P. Pfeifer (ed.) Plenum, New York, pp. 103–115.

Sambrook et al. (1989) in *Molecular Cloning: A Laboratory Manual*, Cold Spring Harbor Press, NY, pp. 9.31–9.58, 7.39–7.52.

Köhler and Milstein (1976) "Derivation of specific antibody–producing tissue culture and tumor lines by cell fusion," Eur. J. Immunol. 6:511–519.

Kang et al. (1992) "Highly Sensitive, Specific Detection of $O^6$–Methylguanine, $O^4$–Methylthymine, and $O^4$–Ethylthymine by the Combination of High–Performance Liquid Chromatography Prefractionation, $^{32}$P Postlabeling, and Immunoprecipitation," Cancer Research 52(19):5307–5312.

Fichtinger–Schepman et al. (1985) "Immunochemical Quantitation of Adducts Induced in DNA by cis–Diamminedichloroplatinum(II) And Analysis of Adduct–Related DNA–Unwinding," Chemico–Biological Interactions 55(3):275–288.

Chadwick et al. (1995) "The detection of cyclobutane thymine dimers, (6–4) photolesions and the Dewar photoisomers in sections of UV–irradiated human skin using specific antibodies, and the demonstration of depth penetration effects," J. Photochem. & Photobiol. 28(2):163–170.

Booth et al. (1994) "Class–specific immunoadsorption purification for polycyclic aromatic hydrocarbon–DNA adducts," Carcinogenesis 15:2099–2106.

Sevilla et al. (1997) "Development of Monoclonal Antibodies to the Malondialdehyde–Deoxyguanosine Adduct, Pyrimidopurinone," Chemical Research in Toxicology 10:172–180.

Wang et al. (1994) "Assembly and DNA binding of recombinant Ku (p70/80) autoantigen defined by a novel monoclonal antibody specific for p70/80 heterodimers," J. Cell. Sci. 107:3223–3233.

Lees–Miller et al. (1997) "Absence of p350 Subunit of DNA–Activated Protein Kinase from a Radfiosensitive Human Cell Line," Science 267:1183–1185.

Cherney et al. (1987) "cDNA sequence, protein structure, and chromosomal location of the human gene for poly(AD-P–ribose) polymerase," Proc. Natl. Acad. Sci. U.S.A. 84:8370–8374.

Duriez et al. (1997) "Chracterization of anti–peptide antibodies directed towards the automodification domain and apoptotic fragment of poly(ADP–ribose) polymerase," Biochimica et Biophysica Acta. 1334:65–72.

Kovalsky and Grossman (1994) "The Use of Monoclonal Antibodies for Studying Intermediates in DNA Repair by the *Escherichia coli* Uvr(A)BC Endonuclease," J. Biol. Chem. 269:27421–27426.

Friedberg et al. (1995) in *DNA Repair And Mutagenesis*, ASM Press, Washington, D.C., pp. 192–206.

Sancar and Hearst (1993) "Molecular Matchmakers," Science 259:1415–1420.

Sancar and Sancar (1988) "DNA Repair Enzymes," Ann. Rev. Biochem. 57:29–67.

(List continued on next page.)

*Primary Examiner*—Robert A. Schwartzman
*Attorney, Agent, or Firm*—Medlen & Carroll, LLP

[57] ABSTRACT

The present invention provides methods for the detection and quantitation of any modification of interest in any nucleic acid sequence. In particular, the invention provides methods for detecting and quantitating low levels of modifications of interest in DNA sequences. The methods of the invention take advantage of combining the use of nucleic acid sequence modification-specific molecules which are specific for DNA modifications, of fluorescently labelled proteins which are specific for the nucleic acid sequence modification-specific molecules, of capillary electrophoresis and of laser-induced fluorescence. The methods of the invention are useful for identifying and detecting exposure to carcinogens, in early risk assessment for cancer, and in monitoring of cancer therapy.

24 Claims, 13 Drawing Sheets

OTHER PUBLICATIONS

Thomas et al. (1985) "Amplification and Purification of UvrA, UvrB, and UvrC Proteins of *Escherichia coli*," J. Biol. Chem. 260:9875–9883.

Jin et al. (1997) "Functions of the DNA Dependent Protein Kinase," Cancer Surveys 29:221–261.

Jackson and Jeggo (1995) "DNA double–strand break repair and V(D)J recombination: involvement of DNA–PK," TIBS 20:412–415.

Jeggo et al. (1995) "Meanage à trois: double strand break repair, V(D)J recombination and DNA–PK," BioEssays 17:949–957.

Gottlieb and Jackson (1993) "The DNA–Dependent Protein Kinase: Requirement of DNA Ends and Association with Ku Antigen," Cell 72:131–142.

Weinfeld et al. (1997) "Interaction of DNA–Dependent Protein Kinase and Poly (ADP–ribose) Polymerase with Radiation–Inducted DNA Strand Breaks," Radiation Research 148:22–28.

Lindahl et al. (1995) "Post–translational modification of poly(ADP–ribose) polymerase induced by DNA strand breaks," TIBS 20:405–411.

de Murcia et al. (1994) "Poly(ADP–ribose) polymerase: a molecular nick–sensor," TIBS 19:172–176.

Lautier et al. (1993) "Molecular and biochemical features of poly(ADP–ribose) metabolism" Molec. Cell. Biochem. 122:171–193.

Uchida et al. (1987) "Nucleotide Sequence of a Full–Length cDNA for Human Fibroblast Poly (ADP–Ribose) Polymerase," Biochem. and Biophys. Res. Comm. 148:617–622.

Molinete et al. (1995) "Overproduction of the poly(ADP)ribose polymerase DNA–binding domain blocks alkylation––induced DNA repair synthesis in mammalian cells," EMBO J. 12:2109–2117.

Shah et al. (1995) "Methods for Biochemical Study of Poly(ADP–Ribose) Metabolism in Vitro and in Vivo," Analyt. Biochem. 227:1–13.

Jiricny et al. (1988) "Mismatch–containing oligonucleotide duplexes bound by the *E. coli* mutS–encoded protein," Nucl. Acids Res. 16:7843–7853.

Lishanski et al. (1994) "Mutation detection by mismatch binding protein, MutS, in amplified DNA: Application to the cystic fibrosis gene," Proc. Natl. Acad. Sci. USA 91:2674–2678.

Su and Modrich (1986) "*Escherichia coli* mutS–encoded protein binds to mismatched DNA base pairs," Proc. Natl. Acad. Sci. USA 83:5057–5061.

Xian et al. (1996) "DNA–protein binding assays from a single sea urchin egg: A high–sensitivity capillary electrophoresis method," Proc. Natl. Acad. Sci. USA 93:86–90.

Leadon (1986) "Differential repair of DNA damage in specific nucleotide sequences in monkey cells," Nucl. Acids Res. 14:8979–8995.

Chaudhry and Weinfeld (1995) "The Action of *Escherichia coli* Endonuclease III on Multiply Damaged Sites in DNA," J. Mol. Biol. 249:914–922.

Ljungman (1991) "The Influence of Chromatin Structure on the Frequency of Radiation–Induced DNA Strand Breaks: A Study Using Nuclear and Nucleoid Monolayers," Radiat. Res. 126:58–64.

Ljungman et al. (1991) "DNA–Bound Proteins Contribute Much More than Soluble Intracellular Compounds to the Intrinsic Protection against Radiation–Induced DNA Strand Breaks in Human Cells," Radiat. Res. 127:171–175.

Olivieri et al. (1984) "Adaptive Response of Human Lymphocytes to Low Concentrations of Radioactive Thymidine," Science 223:594–597.

Wolff et al. (1988) "Human lymphocytes exposed to low doses of ionizing radiations become refractory to high doses of radiation as well as to chemical mutagens that induce double–strand breaks in DNA," Int. J. Radiat. Biol. 53:39–47.

Marples and Skov (1996) "Small Doses of High–Linear Energy Transfer Radiation Increase the Radioresistance of Chinese Hamster V79 Cells to Subsequent X Irradiation," Radiat. Res. 146:382–387.

Joiner et al. (1996) "Hypersensitivity to very–low single radiation doses: Its relationship to the adaptive response and induced radioresistance," Mutat. Res. 358:171–183.

Lambin et al. (1996) "Might intrinsic radioresistance of human tumour cells be induced by radiation?" Int. J. Radiat. Biol. 69:279–290.

Marples et al. (1997) "Low dose hyper–radiosensitivity and increased radioresistance in mammalian cells," Int. J. Radiat. Biol. 71:721–735.

Marples and Joiner (1995) "The Elimination of Low–Dose Hypersenstivity in Chinese Hamster V79–379A Cells by Pretreatment with X Rays or Hydrogen Peroxide," Radiat. Res. 141:160–169.

Youngblom et al. (1989) "Inhibition of the adaptive response of human lymphocytes to very low doses of ionizing radiation by the protein synthesis inhibitor cycloheximide," Mutat. Res. 227:257–261.

Seong et al. (1995) "Adaptive Response to Ionizing Radiation Induced by Low Doses of Gamma Rays in Human Cell Lines," Int. J. Radiat. Oncol. Biol. Phys. 33:869–874.

Ikushima et al. (1996) "Radioadaptive response: Efficient repair of radiation–induced DNA damage in adapted cells," Mutat. Res. 358:193–198.

Lehnert and Chow (1997) "Low doses of ionizing radiation induce nuclear activity in human tumour cell lines which catalyses homologous double–strand recombination," Radiat. Environ. Biophys. 36:67–70.

Cadet et al. (1997) "Artifacts Associated with the Measurement of Oxidized DNA Bases," Environmental Health Perspectives 105:1034–1039.

Cheng and Dovichi (1988) "Subattomole Amino Acid Analysis by Capillary Zone Electrophoresis and Laser–Induced Fluorescence," Science 242:562–564.

Haab and Mathies (1995) "Single Molecule Fluorescence Burst Detection of DNA Fragments Separated by Capillary Electrophoresis," Anal. Chem. 67:3253–3260.

Jackim and Norwood (1990) "Separation and Detection of a Benzo[a]pyrene Deoxyguanosyl–5–monophosphate Adduct by Capillary Zone Electrophoresis," J. High. Res. Chrom. 13:195–196.

Perry–O'Keefe et al. (1996) "Peptide nucleic acid pre–gel hybridization: An alternative to Southern hybridization," Proc. Natl. Acad. Sci. USA 93:14670–14675.

Liu et al. (1991) "Capillary Electrophoresis of Amino Sugars with Laser–Induced Fluorescence Detection," Anal. Chem. 63:413–417.

Schultz and Kennedy (1993) "Rapid Immunoassays Using Capillary Electrophoresis with Fluorescence Detection," Anal. Chem. 65:3161–3165.

Shimura and Karger (1994) "Affinity Probe Capillary Electrophoresis: Analysis of Recombinant Human Growth Hormone with a Fluorescent Labeled Antibody Fragment," Anal. Chem. 66:9–15.

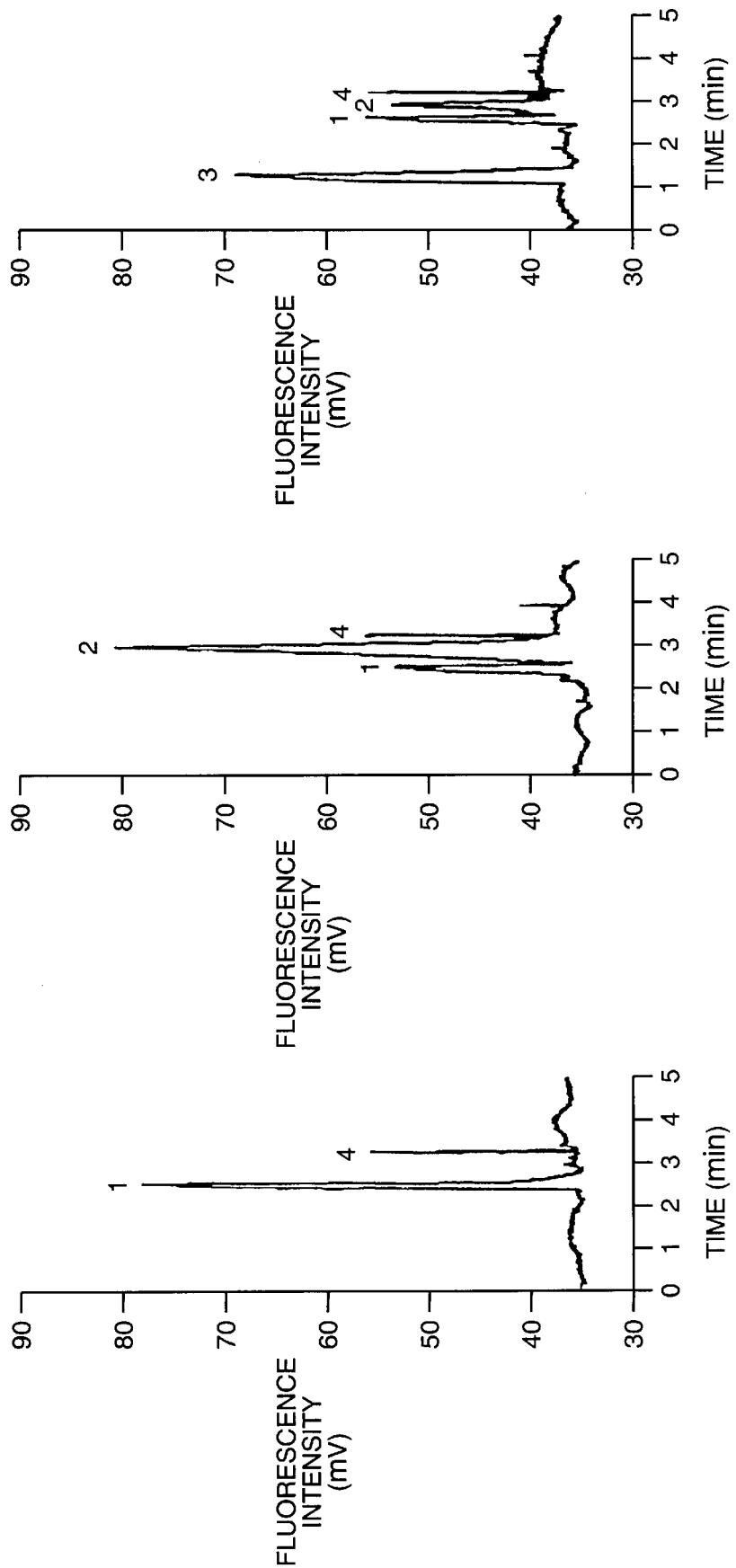

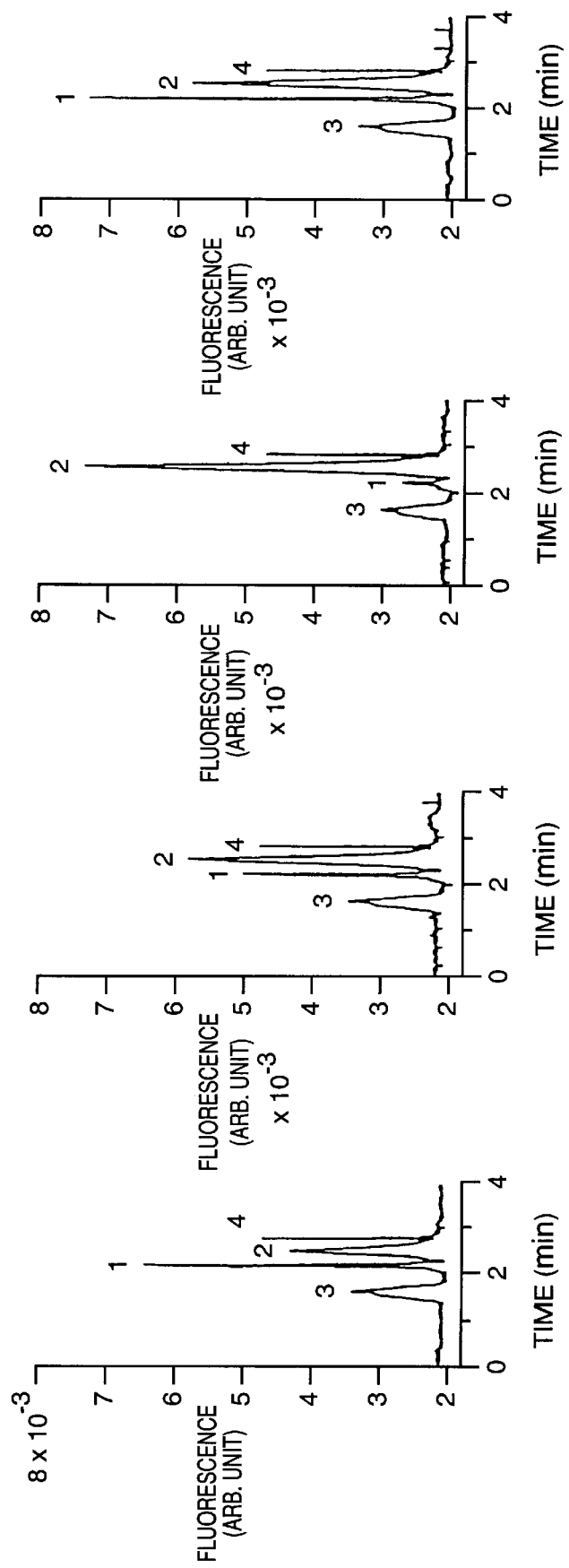

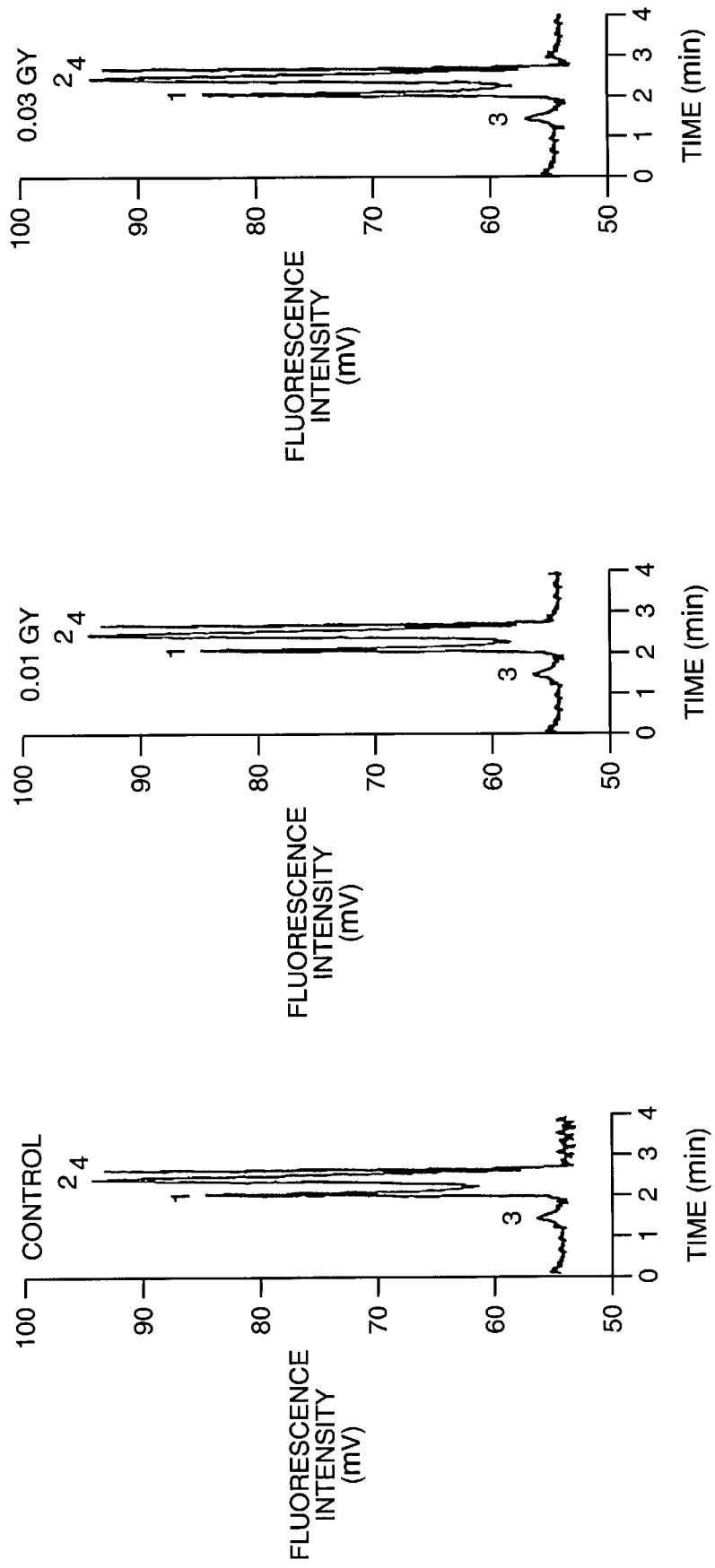

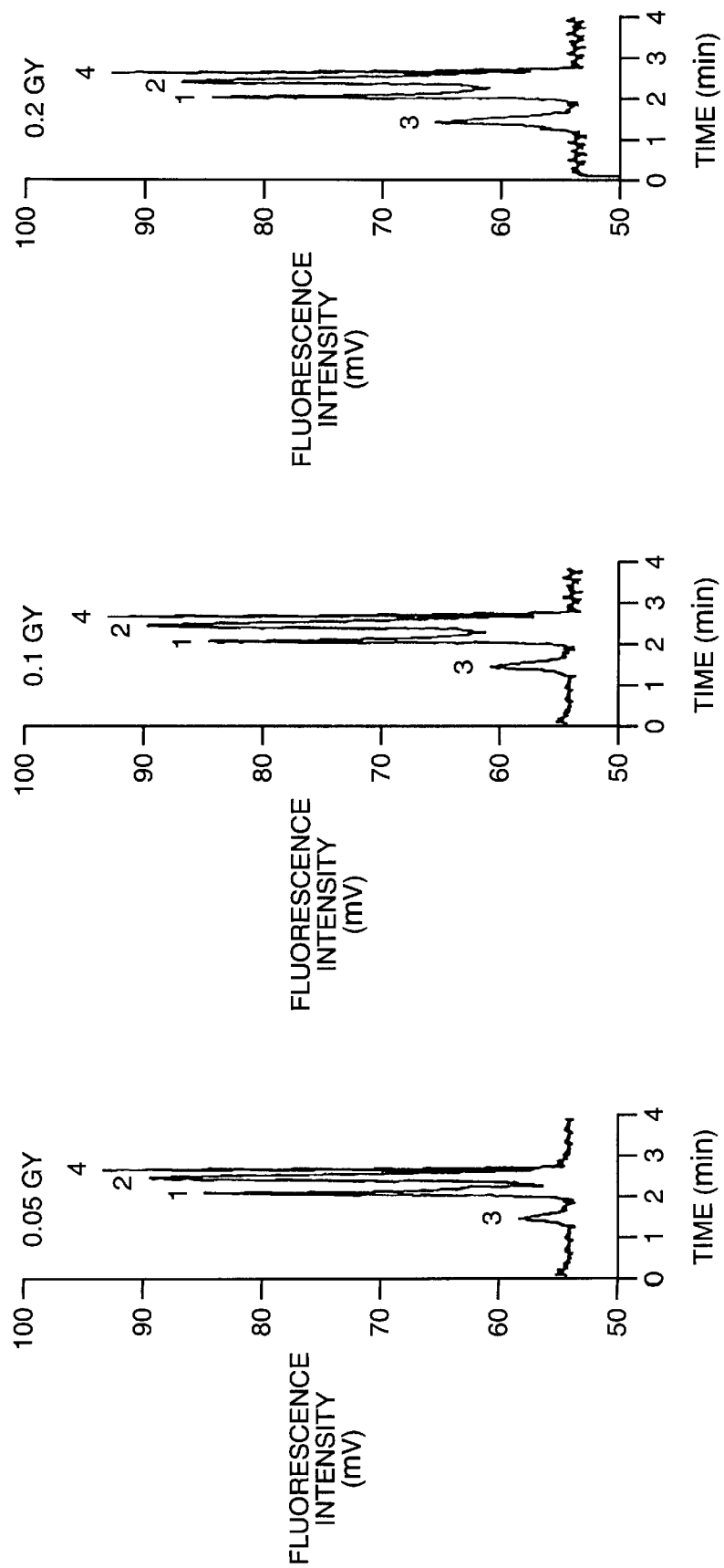

MDKIEVRGARTHNLKNINLVIPRDKLIVVTGLSGSGKSSLAFDT

LYAEGQRRYVESLSAYARQFLSLMEKPDVDHIEGLSPAISIEQKSTSHNPRSTVGTIT

EIHDYLRLLFARVGEPRCPDHDVPLAAQTVSQMVDNVLSQPEGKRLMLLAPIIKERKG

EHTKTLENLASQGYIRARIDGEVCDLSDPPKLELQKKHTIEVVVDRFKVRDDLTQRLA

ESFETALELSGGTAVVADMDDPKAEELLFSANFACPICGYSMRELEPRLFSFNNPAGA

CPTCDGLGVQQYFDPDRVIQNPELSLAGGAIRGWDRRNFYYFQMLKSLADHYKFDVEA

PWGSLSANVHKVVLYGSGKENIEFKYMNDRGDTSIRRHPFEGVLHNMERRYKETESSA

VREELAKFISNRPCASCEGTRLRREARHVYVENTPLPAISDMSIGHAMEFFNNLKLAG

QRAKIAEKILKEIGDRLKFLVNVGLNYLTLSRSAETLSGGEAQRIRLASQIGAGLVGV

MYVLDEPSIGLHQRDNERLLGTLIHLRDLGNTVIVVEHDEDAIRAADHVIDIGPGAGV

HGGEVVAEGPLEAIMAVPESLTGQYMSGKRKIEVPKKRVPANPEKVLKLTGARGNNLK

DVTLTLPVGLFTCITGVSGSGKSTLINDTLFPIAQRQLNGATIAEPAPYRDIQGLEHF

DKVIDIDQSPIGRTPRSNPATYTGVFTPVRELFAGVPESRARGYTPGRFSFNVRGGRC

EACQGDGVIKVEMHFLPDIYVPCDQCKGKRYNRETLEIKYKGKTIHEVLDMTIEEARE

FFDAVPALARKLQTLMDVGLTYIRLGQSATTLSGGEAQRVKLARELSKRGTGQTLYIL

DEPTTGLHFADIQQLLDVLHKLRDQGNTIVVIEHNLDVIKTADWIVDLGPEGGSGGGE

ILVSGTPETVAECEASHTARFLKPML

FIG. 7

MSKPFKLNSAFKPSGDQPEAIRRLEEGLEDGLAHQTLLGVTGSG

KTFTIANVIADLQRPTMVLAPNKTLAAQLYGEMKEFFPENAVEYFVSYYDYYQPEAYV

PSSDTFIEKDASVNEHIEQMRLSATKAMLERRDVVVVASVSAIYGLGDPDLYLKMMLH

LTVGMIIDQRAILRRLAELQYARNDQAFQRGTFRVRGEVIDIFPAESDDIALRVELFD

EEVERLSLFDPLTGQIVSTIPRFTIYPKTHYVTPRERIVQAMEEIKEELAARRKVLLE

NNKLLEEQRLTQRTQFDLEMMNELGYCSGIENYSRFLSGRGPGEPPPTLFDYLPADGL

LVVDESHVTIPQIGGMYRGDRARKETLVEYGFRLPSALDNRPLKFEEFEALAPQTIYV

SATPGNYELEKSGGDVVDQVVRPTGLLDPIIEVRPVATQVDDLLSEIRQRAAINERVL

VTTLTKRMAEDLTEYLEEHGERVRYLRSDIDTVERMEIIRDLRLGEFDVLVGINLLRE

GLDMPEVSLVAILDADKEGFLRSERSLIQTIGRAARNVNGKAILYGDKITPSMAKAIG

ETERRREKQQKYNEEHGITPQGLNKKVVDILALGQNIAKTKAKGRGKSRPIVEPDNVP

MDMSPKALQQKIHELEGLMMQHAQNLEFEEAAQIRDQLHQLRELFIAAS

FIG. 8

MAESSDKLYRVEYAKSGRASCKKCSESIPKDSLRMAIMVQSPMF

DGKVPHWYHFSCFWKVGHSIRHPDVEVDGFSELRWDDQQKVKKTAEAGGVTGKGQDGI

GSKAEKTLGDFAAEYAKSNRSTCKGCMEKIEKGQVRLSKKMVDPEKPQLGMIDRWYHP

GCFVKNREELGFRPEYSASQLKGFSLLATEDKEALKKQLPGVKSEGKRKGDEVDGVDE

VAKKKSKKEKDKDSKLEKALKAQNDLIWNIKDELKKVCSTNDLKELLIFNKQQVPSGE

SAILDRVADGMVFGALLPCEECSGQLVFKSDAYYCTGDVTAWTKCMVKTQTPNRKEWV

TPKEFREISYLKKLKVKKQDRIFPPETSASVAATPPPSTASAPAAVNSSASADKPLSN

MKILTLGKLSRNKDEVKAMIEKLGGKLTGTANKASLCISTKKEVEKMNKKMEEVKEAN

IRVVSEDFLQDVSASTKSLQELFLAHILSPWGAEVKAEPVEVVAPRGKSGAALSKKSK

GQVKEEGINKSEKRMKLTLKGGAAVDPDSGLEHSAHVLEKGGKVFSATLGLVDIVKGT

NSYYKLQLLEDDKENRYWIFRSWGRVGTVIGSNKLEQMPSKEDAIEQFMKLYEEKTGN

AWHSKNFTKYPKKFYPLEIDYGQDEEAVKKLTVNPGTKSKLPKPVQDLIKMIFDVESM

KKAMVEYEIDLQKMPLGKLSKRQIQAAYSILSEVQQAVSQGSSDSQILDLSNRFYTLI

PHDFGMKKPPLLNNADSVQAKVEMLDNLLDIEVAYSLLRGGSDDSSKDPIDVNYEKLK

TDIKVVDRDSEEAEIIRKYVKNTHATTHSAYDLEVIDIFKIEREGECQRYKPFKQLHN

RRLLWHGSRTTNFAGILSQGLRIAPPEAPVTGYMFGKGIYFADMVSKSANYYHTSQGD

PIGLILLGEVALGNMYELKHASHISRLPKGKHSVKGLGKTTPDPSANISLDGVDVPLG

TGISSGVIDTSLLYNEYIVYDIAQVNLKYLLKLKFNFKTSLW

FIG. 9

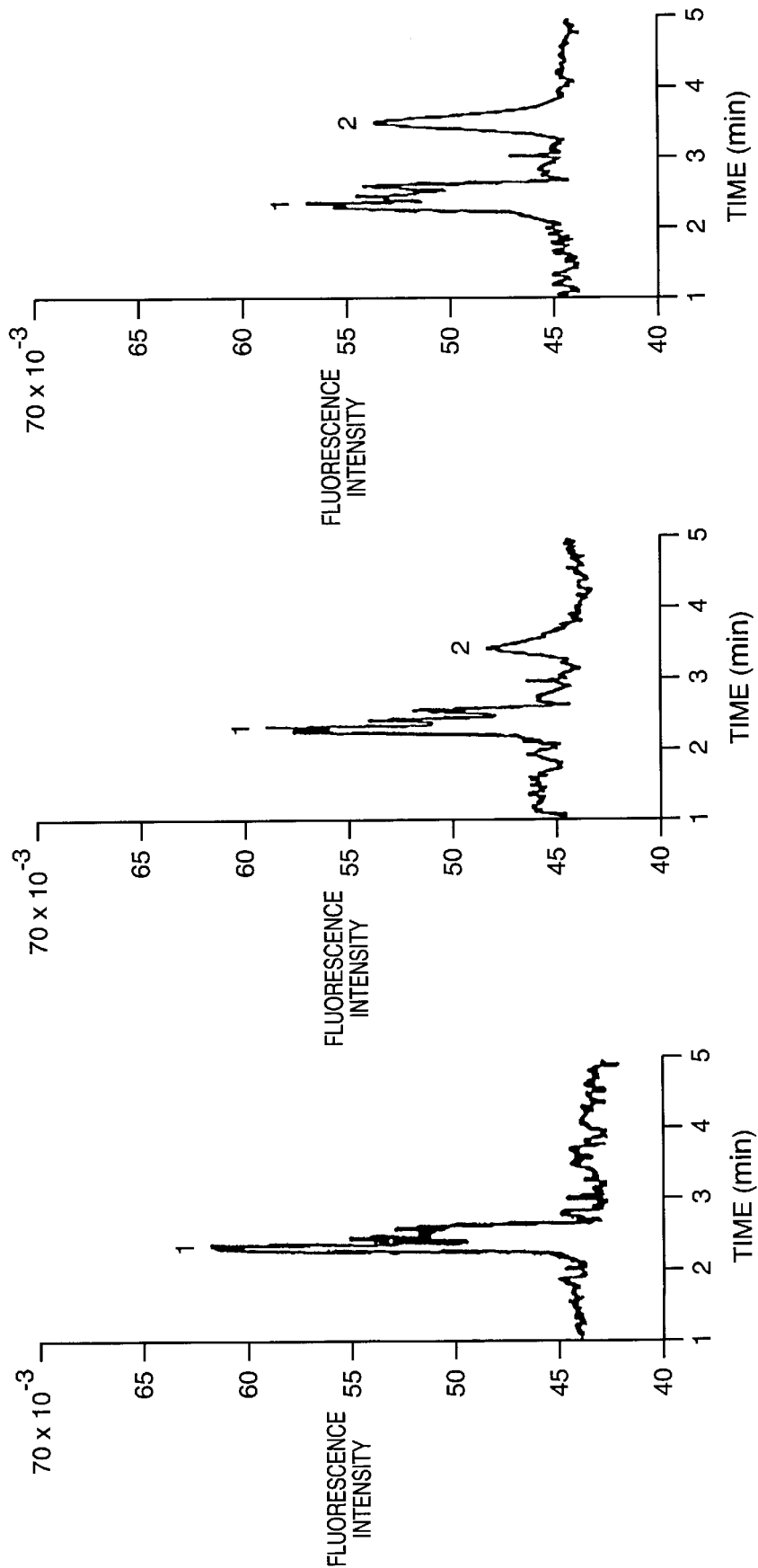

METHODS FOR QUANTITATING LOW LEVEL MODIFICATIONS OF NUCLEOTIDE SEQUENCES

FIELD OF THE INVENTION

The present invention relates to methods for the detection and quantitation of modifictions of nucleic acid sequences. In particular, the invention relates to methods for detecting and quantitating low level modifications of DNA sequences. These methods are useful for identifying and detecting exposure to carcinogens, in risk assessment of cancer, and in monitoring of cancer therapy.

BACKGROUND OF THE INVENTION

A large number of diseases, such as cancer, are associated with genetic modifications, including strand breaks, DNA-adducts, and DNA-protein cross links. Thus, a number of prior art methods have been developed in order to detect and to quantitate modifications in DNA.

Prior art methods for the detection and quantitation of nucleic acid modifications include $^{32}$P-postlabeling [Randerth et al. (1981) Proc. Natl. Acad. Sci. USA 78:6126–6129; Gupta et al. (1996) In Technologies for Detection of DNA Damage and Mutations, G.P. Pfeifer (ed.) Plenum, New York, pp. 45–61], Gas chromatography in combination with mass spectrometry (GC/MS) [Dizdaroglu (1993) FEBS 315:1–6; Niritsin and Markey (1996) Anal. Biochem. 241:35–41], and high-performance liquid chromatography (HPLC) in combination with electrochemical and mass spectrometry detection [Wagner et al. (1992) Proc. Natl. Acad. Sci. 78:3380–3384]. However, these methods suffer from several drawbacks, including poor sensitivity. In addition, these methods also involve a series of chemical derivatization and/or enzymatic hydrolysis and labeling steps which can introduce artifactual DNA lesions, and which require that digestion and labeling reactions be optimized.

Enzyme-linked immunosorbent assays (ELISA) have also been used to detect DNA lesions [Leadon and Hanawlat (1983) Mutat. Res. 112:191–200; Cooper et al. (1997) Science 275:990–993; Melamede et al. (1996) In Technologies for Detection of DNA Damage and Mutations, G.P. Pfeifer (ed.) Plenum, New York, pp. 103–115]. However, these assays require large amounts of starting material (microgram quantities of DNA), and are time consuming. Importantly, all the above-disucussed methods have low sensitivity, and are useful only for detecting greater than femtomole ($10^{-15}$ mole) levels of DNA lesions.

Yet other methods, such as pulse-field gel electrophoresis and single-cell gel electrophoresis, have been employed to detect and measure nucleic acid sequence mutations. While these methods are sensitive, their use is limited to the detection and measurement of strand breaks.

To date, the art has attempted to circumvent the low sensitivity of available methods for detecting and measuring DNA modifications by exposing cells or whole organisms (e.g., rodents) to ionizing radiation or to carcinogenic chemicals at doses which are significantly greater than those doses encountered in the environment or in clinical settings (e.g., clinical ionizing radiation), followed by extrapolating back from the dose-response curves in order to postulate on the effect of environmentally and clinically relevant doses. This approach, however, lacks reliability since the effects of treatment with low and high doses of carcinogens have disparate effects both on DNA lesion formation and on DNA lesion repair.

Thus, what is needed are methods for detecting and measuring modifications of nucleic acid sequences. Preferably, these methods should be sensitive, specific, use small amounts of nucleic acid sequences, and should not require the use of hazardous radioactive compounds, of enzymatic digestion or of chemical derivatization of the nucleic acid substrate.

SUMMARY OF THE INVENTION

The invention provides a method for quantitating at least one modification of interest in a nucleic acid sequence contained in a sample, comprising: a) providing: i) a sample suspected of containing a nucleic acid sequence comprising the at least one modification of interest; ii) a first polypeptide sequence capable of specifically binding to the at least one modification of interest, and iii) a fluorescently labeled second polypeptide sequence capable of specifically binding to the first polypeptide sequence; b) combining the sample, the first polypeptide sequence and the fluorescently labeled second polypeptide sequence to produce a fluorescently labeled second polypeptide sequence:first polypeptide sequence:nucleic acid sequence complex, and a fluorescently labeled second polypeptide sequence:first polypeptide sequence complex; c) separating the fluorescently labeled second polypeptide sequence:first polypeptide sequence:nucleic acid sequence complex, the fluorescently labeled second polypeptide sequence:first polypeptide sequence complex and the fluorescently labeled second polypeptide sequence by capillary electrophoresis; d) detecting the separated fluorescently labeled second polypeptide sequence:first polypeptide sequence:nucleic acid sequence complex by laser-induced fluorescence; and e) quantitating the separated second polypeptide sequence:first polypeptide sequence:nucleic acid sequence complex, thereby quantitating the at least one modification of interest in the nucleic acid sequence.

While it is not intended that the methods of the invention be limited to any particular nucleic acid sequence, in one preferred embodiment, the nucleic acid sequence is a deoxyribonucleic acid sequence. In another preferred embodiment, the nucleic acid sequence is a ribonucleic acid sequence.

The methods of the invention are not intended to be limited to any particular type of modification. However, in one embodiment, the at least one modification of interest is selected from the group consisting of mutation, mismatch, DNA adduct and strand break. In a preferred embodiment, the mutation is selected from the group consisting of deletion, insertion and substitution. In an another preferred embodiment, the strand break is selected from the group consisting of single-strand break and double-strand break. Without limiting the invention to any particular first polypeptide sequence, in a more preferred embodiment, the strand break is a double-strand break and the first polypeptide sequence is DNA-dependent protein kinase. Also without intending to limit the invention to any particular fluorescently labeled second polypeptide sequence, in yet a more preferred embodiment, the fluorescently labeled second polypeptide sequence is a fluorescently labeled antibody capable of specifically binding to the DNA-dependent protein kinase. In an alternative more preferred embodiment, the first polypeptide sequence is poly-(ADP-ribose) polymerase. A yet more preferred embodiment, the fluorescently labeled second polypeptide sequence is a fluorescently labeled antibody capable of specifically binding to the poly(ADP-ribose) polymerase.

Without limiting the invention to a particular first polypeptide sequence, in an alternative more preferred embodiment, the first polypeptide sequence is an antibody. While not limiting the invention to a particular type of antibody, in one more preferred embodiment, the antibody is monoclonal.

While not intending to limit the invention to any particular fluorescently labeled second polypeptide sequence, in one preferred embodiment, the fluorescently labeled second polypeptide sequence is a fluorescently labeled antibody. In a more preferred embodiment, the fluorescently labeled antibody is monoclonal.

It is not intended that the invention be limited to a particular first polypeptide sequence or to a particular fluorescently labeled second polypeptide sequence. However, in one preferred embodiment, the first polypeptide sequence is UvrA, and the fluorescently labeled second polypeptide sequence is fluorescently labeled UvrB. In another preferred embodiment, the first polypeptide sequence is a UvrA:UvrB complex, and the fluorescently labeled second polypeptide sequence is a fluorescently labeled antibody capable of specifically binding to UvrB. In a yet more preferred embodiment, the fluorescently labeled antibody capable of specifically binding to UvrB is monoclonal.

While the methods of the invention are not limited to the order in which the sample, the first polypeptide sequence and the fluorescently labeled second polypeptide sequence are combined, in one preferred embodiment, the combining comprises mixing the sample with the fluorescently labeled second polypeptide sequence to produce a first mixture, followed by mixing the first mixture with the first polypeptide sequence to produce a second mixture.

The invention further provides method for quantitating at least one modification of interest in a nucleic acid sequence contained in a sample, comprising: a) providing: i) a sample suspected of containing a nucleic acid sequence comprising the at least one modification of interest; and ii) a fluorescently labeled polypeptide sequence capable of specifically binding to the at least one modification of interest; b) combining the sample and the fluorescently labeled polypeptide sequence to produce a fluorescently labeled polypeptide sequence:nucleic acid sequence complex; c) separating the fluorescently labeled polypeptide sequence:nucleic acid sequence complex and the fluorescently labeled polypeptide sequence by capillary electrophoresis; d) detecting the separated fluorescently labeled polypeptide sequence:nucleic acid sequence complex by laser-induced fluorescence; and e) quantitating the separated polypeptide sequence:nucleic acid sequence complex, thereby quantitating the at least one modification of interest in the nucleic acid sequence.

BRIEF DESCRIPTION OF THE DRAWINGS

FIG. 2 shows electropherograms from the analysis of four mixtures containing 0.1 ng/μl of BrdU-DNA and varying amounts of primary and secondary antibodies.

FIG. 4 shows representative electropherograms showing the yield of thymine glycol (Tg) in A549 human lung carcinoma cells irradiated with increasing doses (0.01 to 0.2 Gy) from a $^{137}$Cs γ-ray source.

FIG. 7 shows the amino acid sequence (SEQ ID NO:1) of E. coli UvrA protein.

FIG. 8 shows the amino acid sequence (SEQ ID NO:2) of E. coli UvrB protein.

FIG. 9 shows the amino acid sequence (SEQ ID NO:3) of human poly(ADP-ribose) polymerase.

FIG. 10 shows electropherograms showing the separation of fluorescently labeled anti-mouse IgG antibody (peak 1) and the complex of mouse anti-benzo[a]pyrene diol epoxide antibody with fluorescently labeled anti-mouse IgG antibody (peak 2).

DEFINITIONS

Figure 1E:
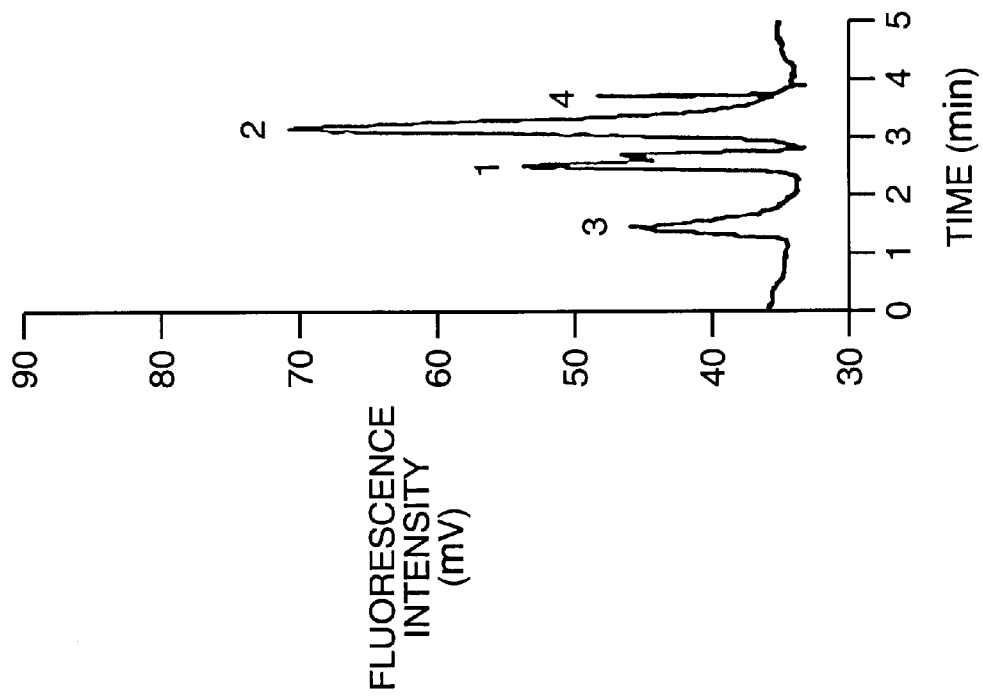
FIG. 1 shows electropherograms showing the separation of fluorescently labeled secondary antibody (peak 1), the complex of primary and secondary antibody (peak 2), and the complex of antigen with primary and secondary antibody (peak 3) in different mixtures.

To facilitate understanding of the invention, a number of terms are defined below.

The terms "amino acid sequence" and "polypeptide sequence" are used interchangeably herein to refer to a sequence of amino acids.

The term "wild-type" when made in reference to a nucleic acid sequence refers to a nucleic acid sequence which has the characteristics of that nucleic acid sequence when isolated from a naturally occurring source. A wild-type nucleic acid sequence is that which is most frequently observed in a population and is thus arbitrarily designed the "normal" or "wild-type" form of the nucleic acid sequence. In contrast, the term "modified nucleic acid sequence" or "mutant nucleic acid sequence" refers to a nucleic acid sequence which displays modifications in sequence and/or functional properties (i.e., altered characteristics) when compared to the wild-type nucleic acid sequence. For example, a mutant nucleic acid sequence refers to a nucleic acid sequence which contains a mutation. It is noted that naturally-occurring mutants can be isolated; these are identified by the fact that they have altered characteristics when compared to the wild-type nucleic acid sequence.

A "modification" as used herein in reference to a nucleic acid sequence refers to any change in the structure of the nucleic acid sequence. Changes in the structure of a nucleic acid sequence include changes in the covalent and non-covalent bonds in the nucleic acid sequence. Illustrative of these changes are point mutations, mismatches, strand breaks, as well as covalent and non-covalent interactions between a nucleic acid sequence, which contains unmodified and/or modified nucleic acids, and other molecules. Illustrative of a covalent interaction between a nucleic acid sequence and another molecule are changes to a nucleotide base (e.g., formation of thumine glycol) and covalent cross-links between double-stranded DNA sequences which are introduced by ultraviolet radiation or by cis-platinum. Yet another example of a covalent interaction between a nucleic acid sequence and another molecule includes covalent binding of two nucleic acid sequences to psoralen following ultraviolet irradiation. Non-covalent interactions between a nucleic acid sequence and another molecule include non-covalent interactions of a nucleic acid sequence with a molecule other than a nucleic acid sequence and other than a polypeptide sequence. Non-covalent interactions between a nucleic acid sequence with a molecule other than a nucleic acid sequence and other than a polypeptide sequence are illustrated by non-covalent intercalation of ethidium bromide or of psoralen between the two strands of a double-stranded deoxyribnucleic acid sequence.

The terms "nucleic acid of interest," "nucleic acid sequence of interest," and "nucleic acid sequence modification of interest" refer to any nucleic acid, any nucleic acid sequence, and any nucleic acid sequence modification, respectively, the detection or manipulation of which may be deemed desirable for any reason by one of ordinary skill in the art.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol.

The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch is present.

The term "strand break" when made in reference to a double stranded nucleic acid sequence includes a single-strand break and/or a double-strand break. A single-strand break refers to an interruption in one of the two strands of the double stranded nucleic acid sequence. This is in contrast to a double-strand break which refers to an interruption in both strands of the double stranded nucleic acid sequence. Strand breaks may be introduced into a double stranded nucleic acid sequence either directly (e.g., by ionizing radiation) or indirectly (e.g., by enzymatic incision at a nucleic acid base).

The terms "nucleic acid" and "unmodified nucleic acid" as used herein refers to any one of the known five nucleic acid bases (i.e., guanine, adenine, cytosine, thymine and uracil). The term "modified nucleic acid" refers to a chemically modified nucleic acid. Illustrative of such modifications would be replacement covalent modifications of the bases, for example alkylation of amino and ring nitrogens as well as saturation of double bonds.

As used herein, the terms "complementary" or "complementarity" are used in reference to "polynucleotides" and "oligonucleotides" (which are interchangeable terms that refer to a sequence of nucleotides) related by the base-pairing rules. For example, for the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

As used herein the term "portion" when in reference to a nucleic acid sequence refers to a fragment of that nucleic acid sequence. The fragments may range in size from 3 nucleotide residues to the entire nucleotide sequence minus one nucleic acid residue.

The terms "Southern blot" and "Southern analysis" refer to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligo-deoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists [J. Sambrook et al. (1989) *Molecular Cloning: A Laboratory Manual,* Cold Spring Harbor Press, NY, pp 9.31–9.58].

The terms "Northern blot" and "Northern analysis" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligo-deoxyribonucleotide probe or DNA probe to detect RNA species complementary to the probe used. Northern blots are a standard tool of molecular biologists [J. Sambrook, J. et al. (1989) supra, pp 7.39–7.52].

The terms "reverse Northern blot" and "reverse Northern analysis" as used herein refer to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligo-ribonuclotide probe or RNA probe to detect DNA species complementary to the ribo probe used.

The terms "specific binding" or "specifically binding" when used in reference to the interaction of a polypeptide with the same or another polypeptide means that the interaction is dependent upon the presence of a particular structure on the interacting same or another polypeptides; in other words the polypeptide is recognizing and binding to a specific polypeptide structure rather than to polypeptides in general. For example, if a polypeptide is specific for structure "A", the presence of a polypeptide containing structure A (or free, unlabelled A) in a reaction containing labelled "A" and the polypeptide will reduce the amount of labelled A bound to the polypeptide.

The terms "specific binding" or "specifically binding" when used in reference to the interaction of a polypeptide sequence with a nucleic acid sequence means that the interaction is dependent upon the presence of a particular structure on or within the nucleic acid sequence; in other words the polypeptide is recognizing and binding to a specific structure on or within the nucleic acid sequence rather than to nucleic acids or to nucleic acid sequences in general. For example, if a polypeptide is specific for structure "A", the presence of a nucleic acid sequence containing structure A (or free, unlabelled A) in a reaction containing labelled "A" and the polypeptide will reduce the amount of labelled A bound to the polypeptide.

The term "polyclonal antibody" refers to an antibody produced from more than a single clone of plasma cells; in contrast "monoclonal antibody" refers to an antibody produced from a single clone of plasma cells. Polyclonal antibodies may be obtained by immunizing a host organism with an immunogen and the resulting antibodies may be isolated from other proteins by using an affinity column, having an Fc binding moiety, such as protein A, or the like. Monoclonal antibodies can be obtained by various techniques familiar to those skilled in the art. Briefly, spleen cells from an animal immunized with a desired antigen are immortalized, commonly by fusion with a myeloma cell [see, Kohler and Milstein (1976) Eur. J. Immunol. 6:511–519; J. Goding (1986) In "Monoclonal Antibodies: Principles and Practice," Academic Press, pp 59–103]. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host. Various techniques useful in these arts are discussed, for example, in Harlow and Lane, (1988) "Antibodies: A Laboratory Manual," Cold Spring Harbor, New York, including: immunization of animals to produce immunoglobulins; production of monoclonal antibodies; labeling immunoglobulins for use as probes; immunoaffinity purification; and immunoassays.

The term "poly-(ADP-ribose) polymerase" when made in reference to a polypeptide sequence refers to at least a DNA binding domain of a polypeptide sequence which is at least 50%, more preferably at least 70%, and most preferably at least 90%, homologous to the DNA binding domain of the amino acid sequence of FIG. 9.

The term "sample" as used herein is used in its broadest sense and includes environmental and biological samples. Environmental samples include material from the environment such as soil and water. Biological samples may be animal (e.g., human), fluid (e.g., blood, plasma and serum), solid (e.g., stool), tissue, liquid foods (e.g., milk), and solid foods (e.g., vegetables). A biological sample suspected of containing a nucleic acid sequence of interest may comprise a cell, tissue extract, body fluid, chromosomes or extrachromosomal elements isolated from a cell, genomic DNA, RNA, cDNA and the like.

DESCRIPTION OF THE INVENTION

The invention provides accurate, specific, and sensitive methods for detecting and for quantitating low levels of any nucleic acid sequence modification of interest in any nucleic acid sequence. The methods of the invention take advantage of combining the use of proteins which are specific for nucleic acid sequence modification (i.e., "nucleic acid sequence modification-specific molecules"), of fluorescently labelled proteins which are specific for the nucleic acid sequence modification-specific molecules, of capillary electrophoresis and of laser-induced fluorescence techniques.

The methods of the invention provide three levels of accuracy and specificity. The first level of accuracy and specificity of the methods of the invention is achieved through the use of proteins which are specific for a nucleic acid sequence modification of interest (i.e., "nucleic acid sequence modification-specific molecule"), and which allow selective recognition of modified nucleic acids as compared to wild-type nucleic acids. These nucleic acid sequence modification-specific molecules bind to the nucleic acid modification of interest to form a nucleic acid sequence modification-specific molecule:nucleic acid sequence complex.

The second level of accuracy and specificity in detection and quantitation of nucleic acid modifications of interest is offered by the use of fluorescently labelled proteins which are specific for the nucleic acid sequence modification-specific molecules. The fluorescent proteins indirectly fluorescently label the nucleic acid modification of interest by specifically binding to the nucleic acid sequence modification-specific molecule:nucleic acid sequence complex.

Yet a third level of accuracy and specificity is provided by the use of capillary electrophoresis to separate free fluorescently labelled protein, fluorescently labelled protein:nucleic acid sequence modification-specific molecule complex, fluorescently labelled protein:nucleic acid sequence modification-specific molecule:nucleic acid sequence complex, the unlabelled wild-type nucleic acid sequence, unlabelled mutant nucleic acid sequence, unlabelled free nucleic acid sequence modification-specific molecule, and unlabeled nucleic acid sequence modification-specific molecule:nucleic acid sequence complex.

Importantly, the methods of the invention are more accurate than prior art methods since they avoid potential artifacts which are caused by chemical or enzymatic nucleic digestion. Instead, the methods of the invention limit sample manipulation to extraction of nucleic acid sequences, incubation of the extracted nucleic acid sequences with proteins which are specific for the nucleic acid modification of interest and with nucleic acid sequence modification-specific molecules, and capillary electrophoresis.

The methods of the invention are also highly sensitive. High sensitivity is provided by the use of laser-induced fluorescence for detection of the separated fluorescently labelled molecular entities. The methods of the invention are highly sensitive, detecting zeptomole ($10^{-21}$ mole) levels of nucleic acid modifications, thus offering a sensitivity which is four to five orders of magnitude (i.e., ten thousand to one hunderd thousand times) greater than that of prior art methods. This enhanced sensitivity makes the methods of the invention particularly useful for the early diagnosis of diseases which are known or believed to be associated with nucleic acid mutations (e.g., cancer, genetic disorders in fetuses in utero, etc.), for monitoring the efficacy of protocols aimed at preventing or treating diseases which are associated with nucleic acid mutations, as well as for evaluating potential exposure to carcinogens (e.g., radiation, chemicals, etc.).

In addition to their high accuracy, specificity and sensitivity as discussed supra, the methods of the invention require only nanogram amounts of nucleic acid sample. This is in contrast to the microgram amounts of nucleic acid sample which are required by prior art methods. The need for only small quantities of starting material make the methods of the invention particularly useful for use with, for example, biopsies and body fluids (e.g., blood).

Furthermore, the methods of the invention do not require the use of hazardous radioactive compounds. Moreover, the methods of the invention are faster than prior art methods which require lengthy and extensive enzymatic digestion of nucleic acids.

The invention is further described under (A) Detecting Modifications In Nucleotide Sequences, (B) Quantitating Modifications In Nucleotide Sequences, (C) Proteins Specific For Nucleic Acid Modifications, (D) Fluorescently Labelled Antibodies, (E) Separation By Capillary Electrophoresis, and (F) Detection By Laser-Induced Fluorescence.

A. Detecting Modifications In Nucleotide Sequences

The methods provided herein are useful for detecting any modification of interest in any nucleic acid sequence. The invention discloses the detection of the illustrative bromodeoxyuridine (BrdU) in pUC18 plasmid DNA (Example 1), of thymine glycol in naked calf thymus DNA and in genomic DNA of irradiated A549 human lung carcinoma cells (Example 2), of mismatches and mutations (Example 3), of benzo[a]pyrene diol epoxide in calf thymus DNA and in genomic DNA of cells treated with benzo[a]pyrene (Example 4), of cyclobutane pyrimidine dimers, 6,4-photoproducts, benzo[a]pyrene adducts, dimethylbenzanthracene adducts, cis-platinum adducts, aflatoxin adducts, psoralen adducts, anthramycin adducts, mitomycin C adducts, N-acetoxy-2-aminofluorene adducts, and N-hydroxy-2-aminofluorene adducts (Example 5), and of single-strand and double-strand DNA breaks (Example 6).

However, the methods of the invention are not limited to detecting modifications of interest in deoxynucleic acid sequences. Rather, the methods of the invention are contemplated to encompass any nucleic acid sequence. "Nucleic acid sequence" and "nucleotide sequence" as used herein refer to an oligonucleotide strand or polynucleotide strand of deoxyribonucleic acid and an oligonucleotide strand or polynucleotide strand of ribonucleic acid. The nucleic acid sequence may be of genomic or synthetic origin, may be single- or double-stranded, and may represent the sense or antisense strand. The nucleic acid sequence may also be contained in a cell or be "naked," i.e., not contained in a cell.

Furthermore, while the invention discloses the detection of bromodeoxyuridine and of thymine glycol, the methods of the invention are not intended to be limited to any particular type of modification. Instead, the methods provided herein are expressly contemplated to include within their scope any modification of interest, so long as a protein which is capable of specifically binding to the modification of interest may be produced.

The methods of the invention include incubating a sample suspected of containing a nucleic acid sequence which contains a modification of interest with a protein that is capable of specifically binding to the nucleic acid modification of interest (i.e., "nucleic acid sequence modification-specific molecule") under conditions such that a nucleic acid sequence modification-specific molecule:nucleic acid complex is produced. Determination of these conditions is within the ordinary skill in the art. For example, one of skill in the art appreciates that such conditions include the use of buffers having similar compositions and pH to those present in physiological conditions.

Detection of the nucleic acid modification of interest may be achieved by indirectly labelling the nucleic acid modification of interest with a fluorescent label which allows for high sensitivity laser-induced fluorescence detection. Indirect labelling of a nucleic acid modification of interest may be achieved by, for example, using a nucleic acid sequence modification-specific molecule which is fluorescently labeled. Detection of the presence and quantity of the fluorescently labeled nucleic acid sequence modification-specific molecule:nucleic acid sequence complex indicates the presence and the quantity of the modification of interest in the nucleic acid sequence.

More preferably, the nucleic acid modification of interest may be fluorescently labeled by mixing the nucleic acid sequence modification-specific molecule with the nucleic acid sequence that contains a modification of interest under conditions such that a nucleic acid sequence modification-specific molecule:nucleic acid sequence complex is produced. The nucleic acid sequence modification-specific molecule:nucleic acid sequence complex is allowed to bind to a fluorescently labelled protein which specifically binds to the nucleic acid sequence modification-specific molecule in order to generate a fluorescently labeled protein:nucleic acid sequence modification-specific molecule:nucleic acid sequence complex. Detection of the presence and the quantity of the fluorescently labeled protein:nucleic acid sequence modification-specific molecule:nucleic acid sequence complex indicates the presence of and the quantity of the modification of interest in the nucleic acid sequence.

It is not intended that the methods of the invention be limited to the use of a fluorescent protein which binds directly to a nucleic acid sequence modification-specific molecule. Rather, the methods of the invention include within their scope the use of fluorescent proteins which bind indirectly (i.e., via one or more intervening molecules such as polypeptide sequences) to nucleic acid sequence modification-specific molecules, so long as the indirect binding of the fluorescently labelled proteins to the nucleic acid sequence modification-specific molecule is specific. For example, the UvrA/UvrB protein complex is a nucleic acid sequence modification-specific molecule complex which specifically binds to a wide range of modified DNA sequences which result from ultraviolet irradiation and chemical carcinogens such as, for example, cyclobutane pyrimidine dimers and benzopyrene adducts. Cyclobutane pyrimidine dimers and benzopyrene adducts in DNA molecules may be detected by specifically and indirectly binding fluorescently labelled UvrB protein to UvrA:DNA complexes, or by specifically and indirectly binding fluorescently labelled mouse anti-UvrB antibody to UvrB:UvrA:DNA complexes.

One of skill in the art appreciates that optimum concentrations of the nucleic acid sequence modification-specific molecule and of the fluorescently labelled protein are essential to the sensitivity and accuracy of quantitation of the modification of interest. An optimum concentration of the nucleic acid sequence modification-specific molecule is a concentration which contains an amount of the nucleic acid sequence modification-specific molecule which at least saturates the amount of nucleic acid modification of interest in the sample. An optimum concentration of the fluorescently labelled protein is a concentration that contains an amount of fluorescently labelled protein which at least saturates the amount of nucleic acid sequence modification-specific molecule in the sample.

Optimum concentrations of the nucleic acid sequence modification-specific molecule and of the fluorescently labelled protein may be empirically determined by the following approach as a guide in which the nucleic acid sequence containing a modification of interest is a DNA sequence, the modification of interest is bromodeoxyuridine (BrdU), the nucleic acid sequence modification-specific molecule which is specific for BrdU is mouse monoclonal antibody to BrdU, and the fluorescently labelled protein which is specific for the nucleic acid sequence modification-specific molecule is fluorescently labeled anti-mouse IgG antibody. A constant amount of DNA sequence which contains a constant amount of BrdU is mixed with varying ratios of the anti-BrdU antibody and the fluorescently labeled anti-mouse IgG. The resulting mixture is expected to contain the following molecular entities: unlabelled DNA containing BrdU, unlabelled free anti-BrdU antibody, unlabeled anti-BrdU:BrdU-containing DNA complex, fluorescently labelled free anti-mouse IgG antibody, fluorescently labelled anti-mouse IgG antibody:anti-BrdU antibody complex, and fluorescently labelled anti-mouse IgG antibody:anti-BrdU antibody:BrdU-containing DNA complex. These molecular entities are separated using capillary electrophoresis, and fluorescence of the three fluorescently labelled molecular entities (i.e., fluorescently labelled free anti-mouse IgG antibody, fluorescently labelled anti-mouse IgG antibody:anti-BrdU antibody complex, and fluorescently labelled anti-mouse IgG antibody:anti-BrdU antibody:BrdU-containing DNA complex) is quantitated using laser-induced fluorescence as described below.

An optimum concentration of the anti-BrdU antibody is achieved when the fluorescence intensity of the fluorescently labelled anti-mouse IgG antibody:anti-BrdU antibody:BrdU-containing DNA complex remains unaltered (ie., does not increase) following an increase in the amount of the anti-BrdU antibody in relation to the total amount of anti-mouse IgG or in relation to the total amount of DNA containing BrdU. This is illustrated by, for example, traces (a) and (b) of FIG. 2 which show electropherograms of samples in which optimum concentrations of anti-BrdU antibody are present. In contrast, trace (c) of FIG. 2 shows an electropherogram of a sample in which the concentration of anti-BrdU antibody is not optimum.

An optimum concentration of the anti-mouse IgG antibody is achieved when the fluorescence intensity of the fluorescently labelled free anti-mouse IgG antibody is, for example, equal to or greater than the fluorescence intensity of the fluorescently labelled anti-mouse IgG antibody:anti-BrdU antibody complex. This is illustrated by the exemplary traces (a), (b) and (d) of FIG. 2 which show electropherograms of samples in which optimum concentrations of anti-mouse IgG antibody are present. In contrast, trace (c) of FIG. 2 shows electropherograms of samples in which the concentration of anti-mouse IgG antibody is not optimum.

One of skill in the art also appreciates that the order in which the nucleic acid sequence which contains a modification of interest, the nucleic acid sequence modification-specific molecule, and the fluorescently labelled protein which specifically binds to the nucleic acid sequence modification-specific molecule are mixed may be important. It is preferred that the nucleic acid sequence which contains the modification of interest is mixed with the fluorescently labelled protein which specifically binds to the nucleic acid sequence modification-specific molecule prior to the addition of the nucleic acid sequence modification-specific molecule.

B. Quantitating Modifications In Nucleotide Sequences

The invention further provides methods for quantitating any modification of interest in any nucleic acid sequence. These methods are exemplified by the quantitation of BrdU in pUC18 plasmid DNA (Example 1), of thymine glycol in naked calf thymus DNA and in genomic DNA of irradiated A549 human lung carcinoma cells (Example 2), of mismatches and mutations (Example 3), of benzo[a]pyrene diol epoxide in calf thymus DNA and in genomic DNA of cells treated with benzo[a]pyrene (Example 4), of cyclobutane pyrimidine dimers, 6,4-photoproducts, benzo[a]pyrene adducts, dimethylbenzanthracene adducts, cis-platinum adducts, aflatoxin adducts, psoralen adducts, anthramycin adducts, mitomycin C adducts, N-acetoxy-2-aminofluorene adducts, and N-hydroxy-2-aminofluorene adducts (Example 5), and of single-strand and double-strand DNA breaks (Example 6).

Quantitation of a modification of interest in a nucleic acid sequence includes the same steps and considerations (i.e., optimum concentrations of the nucleic acid sequence modification-specific molecule, optimum concentration of the fluorescently labelled protein, and order of mixing of the nucleic acid sequence which contains a modification of interest with the nucleic acid sequence modification-specific molecule, and with the fluorescently labelled protein which specifically binds to the nucleic acid sequence modification-specific molecule) as those for the invention's methods for the detection of a modification of interest in a nucleic acid sequence, as discussed supra, with the additional step of quantitating the fluorescently labelled protein:nucleic acid sequence modification-specific molecule:nucleic acid sequence complex.

Quantitation of the fluorescently labelled protein:nucleic acid sequence modification-specific molecule:nucleic acid sequence complex is based on the art-accepted general principle that the intensity of a fluorescence signal is proportional to the quantity of the fluorescent analyte. Quantification of a modification of interest in a nucleic acid sequence is achieved by measuring the fluorescence intensity of the fluorescently labelled protein:nucleic acid sequence modification-specific molecule:nucleic acid sequence complex and calibrating against the fluorescence intensity of standards prepared using known amounts of the same modification of interest in the presence of the same nucleic acid sequence modification-specific molecules and the same fluorescent protein. Alternatively, quantitation of a modification of interest in a nucleic acid sequence may be achieved by measuring the fluorescence intensity of the fluorescently labelled protein:nucleic acid sequence modification-specific molecule:nucleic acid sequence complex and calibrating against the fluorescence intensity of standards prepared using known amounts of a different modification (e.g., BrdU) in the presence of a protein which specifically binds to the different modification (e.g., mouse anti-BrdU antibody) and of the same fluorescently labelled protein (e.g., fluorescently labeled anti-mouse IgG antibody). These methods are further discussed below.

i. Calibration Against Known Amounts Of Specific DNA Modifications

A specific modification of interest in a nucleic acid sequence may be quantitated using, as a standard, nucleic acid sequences which contain the same modification of interest. For example, DNA adducts as well as carcinogenic compounds which cause the formation of such adducts are commercially available from, for example, the National Cancer Institute Carcinogen Reference Standard Repository, Midwest Research Institute, Kansas City, Mo. A catalog containing many carcinogenic compounds and their DNA adducts can be downloaded from http://www.mriresearch.org/ls/nci/intro.html#DOWNLOAD.

Samples in which a nucleic acid modification of interest is to be quantitated and standards which contain known amounts of the same modification of interest are mixed with optimum amounts of a nucleic acid sequence modification-specific molecule and with optimum amounts of a fluorescent protein which specifically binds to the nucleic acid sequence modification-specific molecule. The fluorescent molecular entities are separated by capillary electrophoresis, and the fluorescence intensity of each of the separated entities is measured by laser-induced fluorescence. The quantity of modification of interest in the sample may be determined by extrapolating the fluorescence intensity of the fluorescent protein:nucleic acid sequence modification-specific molecule:nucleic acid sequence complex in the sample to a standard curve of fluorescent intensity of the fluorescent protein:nucleic acid sequence modification-specific molecule:nucleic acid sequence complex present in standard solutions which contain known amounts of the same modification of interest.

ii. Calibration Against Known Amounts Of Bromodeoxyuridine (BrdU)

A specific modification in a nucleic acid sequence may alternatively be quantitated using, as a standard, a nucleic acid sequence which contains a modification which is different from the modification of interest in the nucleic acid sequence. For example, plasmid DNA which contains known amounts of bromodeoxyuridine (BrdU) may be used as a standard to quantitate any modification of interest in any nucleic acid sequence.

Samples which contain a nucleic acid sequence with an unknown amount of a modification of interest are treated with optimum amounts of a nucleic acid sequence modification-specific molecule (e.g., mouse antibody against the modification of interest) and with optimum amounts of a fluorescently labelled protein which specifically binds to the nucleic acid sequence modification-specific molecule (e.g., fluorescently labelled anti mouse IgG antibody). Standards which contain plasmid DNA with known amounts of BrdU are treated with optimum amounts of a protein which specifically binds to BrdU (e.g., monoclonal mouse anti-BrdU antibody) and with optimum amounts of a fluorescently labelled protein which specifically binds to the nucleic acid sequence modification-specific molecule (e.g., fluorescently labelled anti mouse IgG antibody). Fluorescent and non-fluorescent molecular entities are separated by capillary electrophoresis, and the fluorescence intensity of the fluorescent protein:nucleic acid sequence modification-specific molecule:nucleic acid sequence complex in the sample, as well as the fluorescence intensity of the fluorescent anti mouse IgG antibody:mouse anti-BrdU antibody:plasmid DNA complex in the standards is measured using laser-induced fluorescence. The quantity of the modifications of interest in a sample may be determined by extrapolating the fluorescence intensity of the fluorescent protein:nucleic acid sequence modification-specific molecule:nucleic acid sequence complex in the sample to a standard curve of fluorescent intensity of the fluorescent anti mouse IgG antibody:mouse anti-BrdU antibody:plasmid DNA complex present in the standard solutions.

It is preferred, though not required, that the fluorescently labelled protein which specifically binds to the nucleic acid sequence modification-specific molecule be the same as the fluorescently labeled protein which specifically binds to the BrdU-specific protein; the use of the same fluorescently labelled protein both in the sample and in the standards reduces the time, effort and cost of providing a fluorescently labelled protein which is specific for a nucleic acid sequence modification-specific molecule. In addition, because the modification of interest in the sample is saturated with the nucleic acid sequence modification-specific molecule, because BrdU in the standards is saturated with the BrdU-specific protein, and because fluorescence from the same fluorescent protein is measured, the fluorescence intensity from one mole of modification of interest is equal to the fluorescence intensity from one mole of BrdU. Calibration using plasmid DNA which contains known amounts of BrdU is illustrated in Example 2 herein.

C. Proteins Specific For Nucleic Acid Modifications

The specificity of the methods of the invention derives, in part, from the specificity of binding of a protein to the nucleic acid modification of interest. Several proteins which specifically bind nucleic acid sequence modifications are known in the art and may be made either by chemical synthesis or using an expression system.

Chemical synthetic techniques involve, for example, using solid-phase techniques well known in the art. Synthesized polypeptides can be substantially purified by high performance liquid chromatography (HPLC) techniques, and the composition of the purified polypeptide confirmed by amino acid sequencing.

Alternatively, proteins which specifically bind nucleic acid sequence modifications may be produced by molecular biology techniques in an expression system using methods well known in the art. For example, expression of proteins which specifically bind nucleic acid sequence modifications may be accomplished by inserting nucleotide sequences which encode the polypeptide sequence of the proteins which specifically bind nucleic acid sequence modifications into appropriate vectors to create expression vectors, and transfecting the expression vectors into host cells.

Expression vectors can be constructed using techniques well known in the art [Sambrook et al. (1989) *Molecular Cloning, A Laboratory Manual*, Cold Spring Harbor Press, Plainview N.Y.; Ausubel et al. (1989) *Current Protocols in Molecular Biology*, John Wiley & Sons, New York N.Y.]. Briefly, the nucleic acid sequence of interest is placed in operable combination with transcription and translation regulatory sequences. Regulatory sequences include initiation signals such as start (i.e., ATG) and stop codons, promoters which may be constitutive (i.e., continuously active) or inducible, as well as enhancers to increase the efficiency of expression, and transcription termination signals. Transcription termination signals must be provided downstream from the structural gene if the termination signals of the structural gene are not included in the expression vector. Expression vectors may become integrated into the genome of the host cell into which they are introduced, or are present as unintegrated vectors. Typically, unintegrated vectors are transiently expressed and regulated for several hours (eg., 72 hours) after transfection.

The choice of promoter is governed by the type of host cell to be transfected with the expression vector. Host cells include bacterial, yeast, plant, insect, and mammalian cells. Transfected cells may be identified by any of a number of marker genes. These include antibiotic (e.g., gentamicin, penicillin, and kanamycin) resistance genes as well as marker or reporter genes (e.g., β-galactosidase and luciferase) which catalyze the synthesis of a visible reaction product.

Expression of the gene of interest by transfected cells may be detected either indirectly using reporter genes, or directly by detecting mRNA or protein encoded by the gene of interest. Indirect detection of expression may be achieved by placing a reporter gene in tandem with the sequence encoding the protein which specifically binds nucleic acid sequence modifications under the control of a single promoter. Expression of the reporter gene indicates expression of the tandem protein which specifically binds nucleic acid sequence modifications. It is preferred that the reporter gene have a visible reaction product. For example, cells expressing the reporter gene β-galactosidase produce a blue color when grown in the presence of X-Gal, whereas cells grown in medium containing luciferin will fluoresce when expressing the reporter gene luciferase.

Direct detection of expression of the protein which specifically binds nucleic acid sequence modifications can be achieved using methods well known to those skilled in the art. For example, mRNA isolated from transfected cells can be hybridized to labelled oligonucleotide probes and the hybridization detected. Alternatively, polyclonal or monoclonal antibodies specific for the protein which specifically binds nucleic acid sequence modifications can be used to detect expression of the protein using enzyme-linked immunosorbent assay (ELISA), radioimmunoassay (RIA) and fluorescent activated cell sorting (FACS).

Recombinant proteins which specifically bind nucleic acid sequence modifications which are expressed by the host cell can be purified either from the culture medium, if the expression construct directs its secretion into culture medium, or from the host cell using purification techniques known in the art. For example, a protein which specifically binds nucleic acid sequence modifications may be expressed as a fusion protein with heterologous metal chelating peptides (i.e., polyhistidine tracts) or with protein A domains, and purified on commercially available immobilized metals or immunoglobulins, respectively.

While the methods of the invention are not intended to be limited to any particular protein which is specific for nucleic acid modifications, in a preferred embodiment, the proteins specific for nucleic acid modifications include, for example, antibodies, UvrA and UvrB proteins, DNA-dependent protein kinases, poly(ADP-ribose) polymerases, and MutS Protein. These preferred proteins are further discussed below.

i. Antibodies

Polyclonal and monoclonal antibodies which are specific for nucleic acid modifications are known in the art and are commercially available. It is preferred, though not necessary, that the antibody used for binding to the nucleic acid modification of interest be monoclonal. Monoclonal antibodies which are specific for nucleic acid modifications are commercially available, as exemplified by, but not limited to, anti-BrdU antibody (Calbiochem, San Diego, Calif.). Monoclonal antibodies are also known in the art, such as anti-thymine glycol antibody [Leadon and Hanawalt (1983) Mutation Research 112: 191–200], anti-$O^6$-methylguanine antibody [Kang et al. (1992) Cancer Research 52(19): 5307–5312], anti-cis-Platinum antibody [Fichtinger-Schepman et al. (1985) Chemico-Biological Interactions 55(3): 275–288], anti-UV-dimers antibody [Chadwick et al. (1995) J. Photochem. & Photobiol. 28(2): 163–170], anti-benzo(a)pyrene antibody [Booth et al. (1994) Carcinogenesis 15: 2099–2106], and anti-malondialdehyde antibody [Sevilla et al. (1997) Chemical Research in Toxicology 10: 172–180].

Similarly, antibodies which are specific for nucleic acid sequence modification-specific molecules are also known in the art. For example, antibodies have been raised against the three component polypeptides of DNA-dependent protein kinase [Wang et al. (1994) J. Cell. Sci. 107:3223–3233; Lees-Miller et al. (1997) Science 267: 1183–1185], against poly(ADP-ribose) polymerase [(Cherney et al. (1987) Proc. Natl. Acad. Sci. U.S.A. 84: 8370–8374; Duriez et al. (1997) Biochimica et Biophysica Acta. 1334:65–72], and against UvrB [Kovalsky and Grossman (1994) J. Biol. Chem. 269:27421–27426].

Alternatively, monoclonal antibodies which are specific for any nucleic acid mutation of interest may be generated by various techniques familiar to those skilled in the art. Briefly, animals (e.g., mice) are immunized with nucleic acid sequences containing the mutation of interest, and spleen cells from immunized animals are immortalized, commonly by fusion with a myeloma cell [see, Kohler and Milstein (1976) Eur. J. Immunol. 6:511–519; J. Goding (1986) In "Monoclonal Antibodies: Principles and Practice," Academic Press, pp 59–103]. Immunization with antigen may be accomplished in the presence or absence of an adjuvant, e.g., Freund's adjuvant. One of skill in the art knows that the use of adjuvant may influence the class of antibody produced. Typically, 10 μg antigen in 50–200 μl adjuvant or aqueous solution is administered per mouse by subcutaneous, intraperitoneal or intramuscular routes. Booster immunization may be given at intervals, e.g., 2–8 weeks. The fmal boost is given approximately 2–4 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400× g for 5 min.), washed and counted.

Spleen cells are fused with myeloma cells to generate hybridoma cell lines. Several myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10–15% fetal calf serum. One of skill in the art knows that because most currently available mouse myeloma cell lines used for hybridoma production are of BALB/c origin, the mice used for immunization as well as the mice used as recipients of the resulting hybridomas are preferably of a BALB/c genetic background in order to avoid rejection by the recipient mouse of the hybridomas which display the histocompatibility antigens of the myeloma cells. Fusion of myeloma cells and spleen cells may be accomplished using polyethylene glycol (PEG) or by electrofusion using protocols which are routine in the art. Fused cells are distributed into 96-well plates followed by selection of fused cells by culture for 1–2 weeks in 0.1 ml DMEM containing 10–15% fetal calf serum and HAT. The supernatants are screened for antibody production using methods well known in the art. Hybridoma clones from wells containing cells which produce antibody are obtained, e.g., by limiting dilution. Cloned hybridoma cells (4–5×10$^6$) are implanted intraperitoneally in recipient mice, preferably of a BALB/c genetic background. Sera and ascites fluids are collected from mice after 10–14 days.

ii. UvrA and UvrB Proteins

UvrA and UvrB proteins play a role in damage-specific recognition and in nucleotide excision repair in which UvrA and UvrB proteins interact to form a protein complex which has been shown to specifically locate and bind base damage in the genome [Friedberg et al., in "DNA Repair And Mutagenesis" ASM Press, Washington, D.C. (1995), pp. 192–206; Sancar and Hearst (1993) Science 259:1415–1420; Sancar and Sancar (1988) Ann. Rev. Biochem. 57:29–67]. UvrA protein is a DNA-binding protein which binds DNA containing various forms of base damage, ranging from AP sites to cross-link initiated triple helixes [Friedberg et al. (1995)]. The amino acid sequence (SEQ ID NO:1) of *E. coli* UvrA protein (GenBank Accession No: M13495) is shown in FIG. 7.

UvrB protein interacts specifically with UvrA protein to form stable protein-protein and protein-protein-DNA complexes which are important intermediates in the biochemistry of the damage-specific incision of DNA. The amino acid sequence (SEQ ID NO:2) of *E. coli* UvrB protein (GenBank Accession Nos.: X03678, J01722, J01723, M24329, V00374, V00375) is shown in FIG. 8. The UvrA protein functions as a molecular matchmaker which delivers UvrB protein to sites of distortive base damage in DNA by the formation of a transient $(UvrA)_2(UvrB)_1$-DNA complex from which it rapidly dissociates, leaving a highly stable $UvrB_1$-DNA complex. The UvrA and UvrB proteins may be used to specifically bind modifications of interest in DNA, such as those exemplified by, but not limited to, UV dimers (e.g., cyclobutane pyrimidine dimers and 6,4-photoproducts), polycyclic aromatic hydrocarbon adducts (e.g., benzo(a)pyrene and dimethylbenzanthracene), cis-platinum adducts, aflatoxin adducts, psoralen adducts, anthramycin adducts, mitomycin C adducts, N-acetoxy-2-aminofluorene adducts, and N-hydroxy-2-aminofluorene adducts. For example, UvrA protein, together with fluorescently labeled UvrB protein, may be used specifically to bind to at least one of the above-listed DNA modifications to form a fluorescently labeled UvrB:UvrA:DNA complex. Alternatively, UvrA and UvrB may be used to specifically bind to DNA modifications to form a UvrB:UvrA:DNA complex which is in turn fluorescently labelled with a fluorescent anti-UvrB antibody.

The UvrA and UvrB polypeptide sequences may be produced by an expression system, such as that previously described [Thomas et al. (1985) J. Biol. Chem. 260:9875–9883].

iii. DNA-Dependent Protein Kinase

DNA-dependent protein kinases are eukaryotic proteins which specifically bind to DNA double strand ends, such as those generated following exposure to ionizing radiation and during V(D)J recombination [Jin et al. (1997) Cancer Surveys 29:221–261; Jackson and Jeggo (1995) TIBS 20:412–415; Jeggo and Jackson (1995) BioEssays 17:949–957]. DNA-dependent protein kinase (DNA-PK) is a serine/threonine protein kinase found in the nucleus. It is a heterotrimeric complex consisting of a large catalytic subunit DNA-$PK_{cs}$ and a dimer of 70- and 86-kDa polypeptides known as the Ku autoantigen. The complete complex binds to DNA double-strand breaks but not single-strand breaks [Gottlieb and Jackson (1993) Cell 72: 131–142; Weinfeld et al. (1997) Radiation Research 148: 22–28]. DNA-dependent protein kinase is commercially available (Promega, Madison Wis.) (http://www.promega.com), and the GenBank Accession No. for partial cDNA sequences of the catalytic subunit are U35835 and U63630. DNA-dependent protein kinase may be used to specifically bind to double-strand breaks in DNA.

iv. Poly(ADP-Ribose) Polymerase

Poly(ADP-ribose) polymerase (PARP) is a 116-kDa DNA-binding protein that binds tightly to single-strand breaks and double-strand breaks (e.g., those caused by ionizing radiation or alkylating agents) in the absence of nicotinamide adenine dinucleotide [Lindahl et al. (1995) TIBS 20:405–411; De Murcia et al. (1994) TIBS 19:172–176; Lautier et al. (1993) Molec. Cell. Biochem 122:171–193]. The human poly(ADP-ribose) polymerase cDNA has been cloned and sequenced [Cherney et al. (1987) Proc. Natl. Acad. Sci. U.S.A. 84: 8370–8374; Uchida et al. (1987) Biochemical and Biophysical Research Communications 148: 617–622; GenBank accession numbers M32721, J03030 and M18112). The poly(ADP-ribose) polymerase protein and antibodies thereto are available [Cherney et al. (1987); Duriez et al. (1997)]. The poly(ADP-ribose) polymerase protein may be used to specifically bind double-strand and/or single-strand breaks in DNA. More specifically, the 46-kDa DNA binding domain of PARP has been cloned and overexpressed in a bacterial system [Molinete et al. (1995) EMBO J. 12:2109–2117]. Monoclonal antibodies to the DNA binding domain [Shah et al. (1995) Analyt. Biochem. 227:1–13] are available [Dr. G. G. Poirier, University of LeeVal, Quebec].

V. MutS Protein

The *E. coli* Mut S protein (GenBank Accession No. U69873) binds to several different mismatches [Jiricny et al. (1988) Nucleic Acids Res. 16:7843–7853] and has been used to measure mismatches and mutations [e.g., Lishanski et al. (1994) Proc. Natl. Acad. Sci. USA 91:2674–2678]. The *E. coli* Mut S protein may be made purified from an overproducing strain of *E. coli* [Su and Modrich (1986) Proc. Natl. Acad. Sci. USA 83:5057–5061]. MutS protein is useful for the quantitation of mutations and mismatches.

D. Fluorescently labelled Antibodies

The specificity of the methods of the invention is based, in part, on the binding specificity of fluorescently labelled antibodies for the nucleic acid sequence modification-specific molecule. Polyclonal and monoclonal antibodies which are labelled with various fluorescent labels (e.g., tetramethylrhodamine, fluorescein, Cy3) are commercially available (Calbiochem, San Diego, Calif.; Sigma, St. Louis, Mo.; Cedarlane Laboratories Ltd., Homby, Ontario, Canada; MSRS Catalog http://www.antibodies-probes.com/). Alternatively, polyclonal and monoclonal antibodies may be labelled with a fluorescent label using methods known in the art. Fluorescent labels are commercially available from, for example, Molecular Probes (http://www.probes.com).

E. Separation By Capillary Electrophoresis

The specificity of the methods provided herein is further enhanced by the use of capillary electrophoresis to separate fluorescent and non-fluorescent molecular entities. Capillary electrophoresis is described by Hjerten et al., U.S. Pat. No. 5,114,551, the entire contents of which are hereby incorporated by reference. Capillary electrophoresis includes the use of capillaries which are filled either with a gel (e.g., polyacrylamide) or with buffer. The use of capillary electrophoresis in the methods of the invention provides rapid sample analysis and permits the use of small sample volumes, making it particularly useful for analyzing samples of biological interest [See, e.g., Xian et al. (1996) Proc. Natl. Acad. Sci. USA 93:86–90].

One of skill in the art knows that detection and quantitation of fluorescently labelled protein:nucleic acid sequence modification-specific molecule:nucleic acid sequence complexes require that the complex remain undissociated during the capillary electrophoresis procedure, that protein adsorption to the capillary inner walls be minimized, and that separation of the free entities (e.g., antibodies) and complexes (e.g., fluorescent protein:nucleic acid sequence modification-specific molecule:nucleic acid sequence complex and fluorescent protein:nucleic acid sequence modification-specific molecule complex) in the mixture. These considerations may readily be empirically optimized by one of ordinary skill in the art by, for example, altering the intensity of the electric field, the length and surface properties of the capillary, and the composition (e.g., ionic strength and pH) of separation buffers. For example, while neutral pH of the separation buffer is favorable for the formation of stable fluorescent protein:nucleic acid sequence modification-specific molecule:nucleic acid sequence complexes, the adsorption of proteins onto the capillary at neutral pH is severe. Thus, one of skill in the art appreciates that buffers having a pH of greater than 7.0 generally result in a reduction in protein adsorption to the capillary wall. In addition, dissociation of fluorescent protein:nucleic acid sequence modification-specific molecule:nucleic acid sequence complexes is reduced by maintaining low current and low Joule heating inside the capillary. Adsorption of fluorescent protein:nucleic acid sequence modification-specific molecule:nucleic acid sequence complexes to the capillary is further minimized by treating the capillary with 0.1 M NaOH every 3 to 5 runs to renew the surface and to improve reproducibility.

More specifically, electrophoresis may be driven by a high voltage power supply (CZE1000R, Spellman High Voltage Electronics, Plainview, N.Y., USA). The separation voltage, injection voltage, and injection time may be controlled by a Macintosh computer, with program written in LabVIEW (National Instruments, Austin, Tex., USA). Separation is carried out in 42 cm long, 20 $\mu$m inner diameter, 150 $\mu$m outer diameter, fused silica capillaries (Polymicro Technologies, Phoenix, Ariz., USA) at an electric field of 400 V/cm. The high voltage injection end of the capillary, along with a platinum electrode, is inserted into a sample solution (when injecting sample) or running buffer (when performing separation) and is held in a Plexiglas box equipped with safety interlock. The other end (injection end) of the capillary is grounded. The detection window is 35 cm from the injection end. Samples are electrokinetically injected onto the separation capillary by applying a 1000 V potential for 5 second.

Alternatively, a commercially available capillary electrophoresis system may be used (Beckman Instruments, Inc., http://www.beckman.com; Dionex Corp., http://www.dionex.com; Hewlett-Packard Co., http://www.hp.com/go/chem).

F. Detection By Laser-Induced Fluorescence

Laser-induced fluorescence provides selective and sensitive excitation of a fluorescent analyte of interest. Other non-fluorescent molecular entities and those requiring different excitation frequencies to produce fluorescence do not interfere with the fluorescent signal of the fluorescent analyte of interest. The methods of the invention exploit the sensitivity of laser-induced fluorescence to detect fluorescent molecular entities following separation by capillary electrophoresis.

Methods for laser-induced fluorescence are known in the art, such as those described by Zare et al., U.S. Pat. No. 4,675,300, the entire contents of which are hereby incorporated by reference. For example, laser-induced fluorescence detectors may be constructed using methods known in the art. For example, a laser-induced fluorescence detector may be constructed on an optical table. A 1-mW helium-neon laser (Melles Griot, Nepean, Ontario, Canada) with a wavelength of 543.5 nm, is used as the excitation source. The laser beam is focused with a 6.3x microscope objective onto the capillary detection window. Fluorescence is collected at 900 with respect to both the laser beam and the sample stream by using a high numerical aperture microscope objective (60x, 0.7 NA, Universe Kogaku, Oyster Bay, N.Y., USA). The fluorescence is then spectrally filtered with a bandpass filter (580DF40) to reject scattered laser light. A 200-$\mu$m radius pinhole is placed in the reticle position of the microscope objective to restrict the field of view of the photomultiplier tubes (PMT) to the illuminated sample stream. The fluorescence is detected with a photomultiplier tube (PMT) (R1477, Hamamatsu Photonics, Japan). The output from the PMT is digitized by a PCI data acquisition board and a LabVIEW software (National Instruments, Austin, Tex.) in a Power Macintosh computer.

One of skill in the art appreciates that it is necessary to align a tightly focused laser beam with a small-diameter sample stream so that the fluorescence passes through a high numerical aperture objective and is detected by the PMT. This can be achieved by mounting the capillary detection end and the laser focusing objective each on a set of three-axis translation stages, so that their positions could be adjusted with ease and precision. An auxiliary microscope may be placed opposite the collection optic to assist the alignment. The location of the PMT, the collection optics and the limiting aperture are preferably fixed. All other components are preferably aligned with respect to the collection optics. A commercially available laser-induced fluorescence detector, such as that available from Beckman Instruments Inc., may also be used.

EXPERIMENTAL

The following examples serve to illustrate certain preferred embodiments and aspects of the present invention and are not to be construed as limiting the scope thereof.

EXAMPLE 1

Optimizing Concentrations Of Primary And Secondary Antibodies For Detection And Quantitation of Bromodeoxyuridine In DNA This experiment was conducted to determine the optimum saturating concentrations of a primary antibody which specifically recognizes BrdU lesions in DNA and of a tetramethylrhodamine (TMR) labeled secondary monoclonal anti-mouse antibody. Mouse monoclonal antibodies to bromodeoxyuridine (BrdU) [Leadon (1986) Nucleic Acids Res. 14:8979] were used because we could generate model DNA antigens containing a specified quantity of this modified base, and because mouse monoclonal antibodies to BrdU are commercially available (Calbiochem, San Diego, Calif.). TMR labeled secondary antibodies were used because of the convenient fluorescence wavelength of TMR and because they are also commercially available (Calbiochem, San Diego, Calif.).

For preparation of the antigens, pUC18 plasmid molecules were cleaved with Sal I, the overhanging termini were filled in by incorporation of nucleotides including BrdU, and then the plasmid molecules were ligated [Chaudhry and Weinfeld (1995) J. Mol. Biol. 249:914]. Thus, two molecules of BrdU were incorporated per molecule of pUC18 (2690 bp). Plasmid containing BrdU was mixed with tetramethylrhodamine (TMR) labeled anti-mouse secondary antibody (Calbiochem, La Jolla, Calif.) in 10 mM Tris-HCl buffer (pH 7.3) and anti-bromodeoxyuridine (BrdU) mouse monoclonal antibody. Separation by capillary electrophoresis was carried out in a 42 cm long, 20 $\mu$m inner diameter and 145 $\mu$m outer diameter fused silica capillary at an electric field of 400 V/cm. The detection window was 35 cm from the injection end of the capillary. The separation buffer (pH 10.5) contained 20 mM borate and 10 mM Tris-HCl. Electrokinetically injected sample volume was 1 nanoliter ($10^{-9}$ liter). The electropherograms were obtained by using a lab-built capillary electrophoresis system with laser-induced fluorescence detection, similar to that described previously, except without the use of a sheath flow cuvette.

Figure 1D:
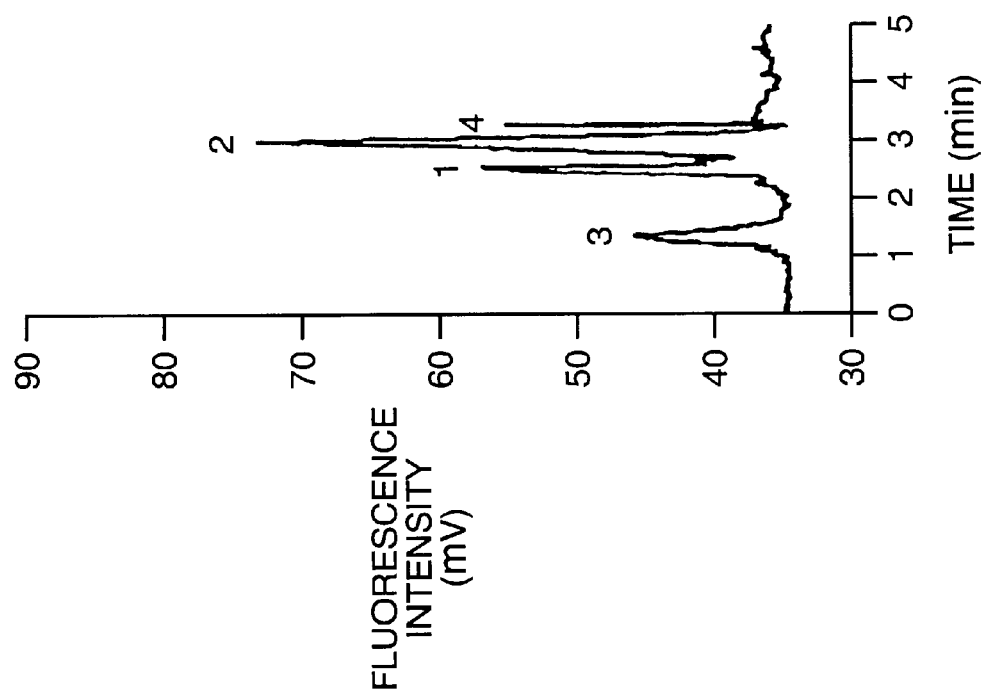

FIG. 1 shows electropherograms showing the separation of fluorescently labeled secondary antibody (peak 1), the complex of primary and secondary antibody (peak 2), and the complex of antigen with primary and secondary antibody (peak 3) in different mixtures. FIG. 1(A) shows 0.8 pg (1 nl of 0.8 pg/ml solution) of tetramethylrhodamine (TMR) labeled anti-mouse secondary antibody (Calbiochem, La Jolla, Calif.) in 10 mM Tris-HCl buffer (pH 7.3); FIG. 1(B) shows a mixture of (A) and 0.4 pg of anti-bromodeoxyuridine (BrdU) mouse monoclonal antibody; FIG. 1(C) shows a mixture of (B) and 0.25 pg of pUC18 plasmid DNA containing BrdU; FIG. 1(D) shows a mixture containing 0.8 pg of TMR labeled anti-mouse secondary antibody, 0.4 pg of anti-BrdU mouse monoclonal antibody, and 0.05 pg of pUC18 plasmid DNA containing BrdU; FIG. 1(E) shows a mixture of (D) and 450 pg of unmodified pUC18 DNA. Peak 4 is due to the free TMR in the secondary antibody reagent solution. The presence of this fluorescent compound in all assays makes it a good internal standard to correct for changes in instrument sensitivity.

Figure 3:
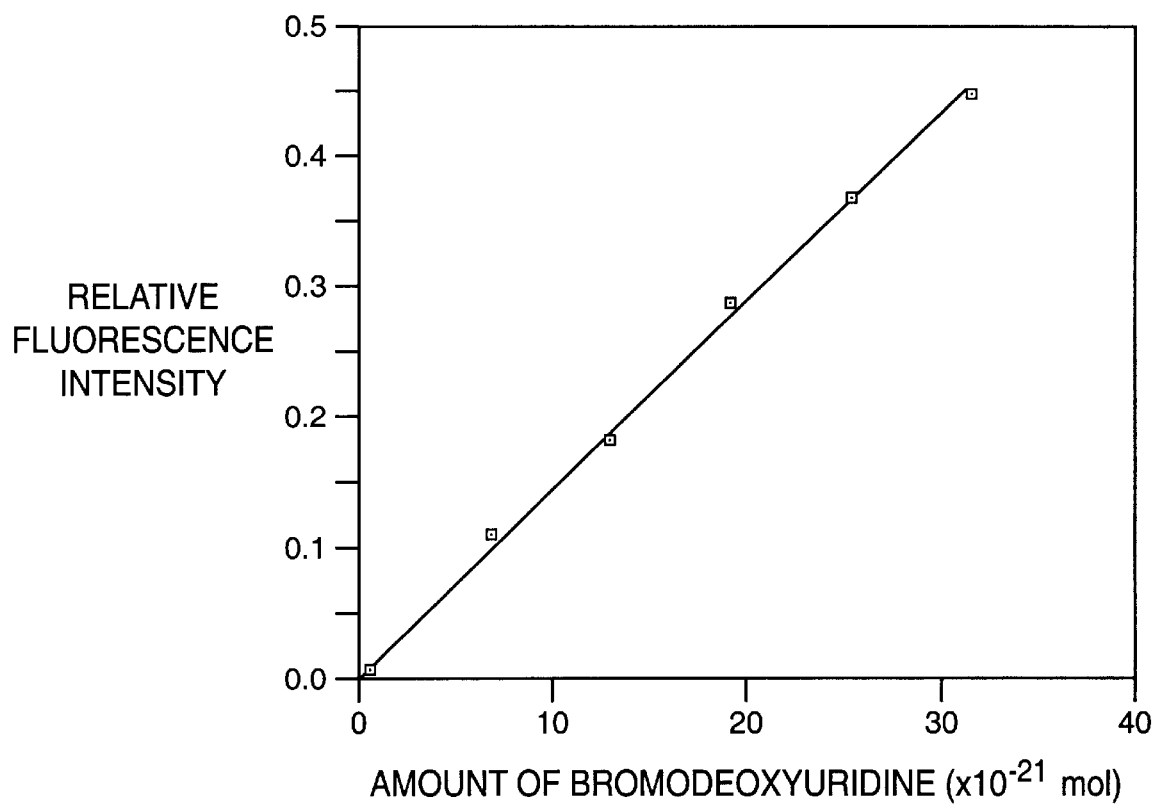
FIG. 3 shows calibration of relative fluorescent intensity of different amounts os BrdU injected into the capillary and measured by laser-induced fluorescence.

The results in FIG. 1 show that capillary electrophoresis separates the unbound secondary antibody (FIG. 1A, peak 1), the complex of secondary and primary antibody (FIG. 1B, peak 2), and the complex of antigen with the primary and secondary antibodies (FIG. 1C, peak 3). The signal in peak 3 (FIG. 1C) was produced by $\sim 3 \times 10^{-19}$ mole of BrdU. This was based on calibration of relative fluorescent intensity of different amounts of BrdU injected into the capillary and measured by laser-induced fluorescence (FIG. 3).

We compared the signals produced by BrdU-containing plasmid DNA at a concentration of 0.05 μg/ml in the absence (FIG. 1D) or presence (FIG. 1E) of 450 μg/ml of unmodified pUC18 DNA, which corresponds to a final ratio of 2 BrdU molecules per $2.42 \times 10^7$ bp. The large excess of undamaged DNA did not alter the signal in peak 3. Since the sample concentration of plasmid DNA antigen was 0.05 μg/ml and a 1-nl aliquot was injected onto the capillary, the signal in peak 3 represents $\sim 6 \times 10^{-20}$ mole of BrdU. The detection limit, based on a signal-to-noise ratio of three, was $3 \times 10^{-21}$ mole, which represents an improvement of 4 to 5 orders of magnitude (i.e., ten thousand to one hunderd thousand times) over currently available assays for DNA base damage.

To confirm that the saturation conditions are reached with both the primary antibody and the fluorescent secondary antibody, mixtures containing 0.1 ng/μl of BrdU-DNA and varying amounts of primary and secondary antibodies were prepared. The mixtures were analyzed by capillary electrophoresis coupled with laser-induced fluorescence detection.

The results are shown in FIG. 2. FIG. 2 shows electropherograms from the analysis of four mixtures containing 0.1 ng/μl of BrdU-DNA and varying amounts of primary and secondary antibodies. FIG. 2(a) contained 0.1 ng/μl of BrdU-DNA, 0.8 ng/μl secondary antibody and 0.2 ng/μl primary antibody; FIG. 2(b) contained 0.1 ng/μl of BrdU-DNA, 0.8 ng/μl secondary antibody and 0.4 ng/μl primary antibody; FIG. 2(c) contained 0.1 ng/μl of BrdU-DNA, 0.8 ng/μl secondary antibody and 0.8 ng/μl primary antibody; FIG. 2(d) contained 0.1 ng/μl of BrdU-DNA, 1.6 ng/μl secondary antibody and 0.4 ng/μl primary antibody. Peak 1 represents secondary antibody (anti-mouse IgG labeled with tetramethylrhodamine); Peak 2 represents the complex of secondary antibody with primary antibody (mouse monoclonal anti-BrdU); Peak 3 represents a complex of antigen (BrdU-DNA) with primary and secondary antibodies; Peak 4 represent free tetramethylrhodamine fluorophore.

The results in FIG. 2 show that as the amount of primary antibody (anti-BrdU) was increased from 0.2 ng/μl (FIG. 2a) to 0.4 ng/μl (FIG. 2b) and to 0.8 ng/μl (FIG. 2c), the peak intensity due to 0.8 ng/μl of fluorescently labeled secondary antibody (peak 1) decreased. Increasing amount of the secondary antibody bound to the primary antibody resulted in the increase of the complex of primary and secondary antibodies (peak 2) and the decrease of the free secondary antibody (peak 1). In the case of FIG. 2c, not enough secondary antibody was present to saturate the primary antibody, which was evident from the reduced intensity of peak 3. When the amount of secondary antibody was increased to 1.6 ng/μl (FIG. 2d), full intensity of the complex peak (peak 3) was restored. Thus, the fluorescence intensity of peak 1 (free secondary antibody) in relation to the fluorescence intensity of peak 2 (complex of secondary and primary antibodies) can be used to indicate whether the primary antibody was saturated with the secondary antibody. When the intensity of peak 1 was, for example, equal to or higher than that of peak 2, the primary antibody was saturated with the secondary antibody.

EXAMPLE 2

Detection And Quantitation Of Thymine Glycol In Irradiated DNA

The following experiments were carried out with antibodies to 5,6-dihydroxy-5,6-dihydrothymine (thymine glycol, Tg) in order to determine a detection limit in terms of radiation dose and to compare the yield of Tg induced in cellular DNA versus naked DNA.

A. Thymine glycol In Irradiated Human Lung Carcinoma Cells

The primary antibodies were mouse monoclonal antibodies against $OsO_4$-treated poly(dT) [Leadon and Hanawalt (1983) Mutat. Res. 112:91], which are highly specific for Tg against a background of unmodified thymine in DNA. Calibration based on BrdU-DNA standards was used to quantify Tg from measured fluorescence intensities. The ratios of the immunoreagents and the antigen (BrdU or Tg) were varied to obtain optimum conditions. In particular, we used an excess of fluorescently labeled secondary antibody to complex with all available primary antibody, and similarly, we maintained an excess of both secondary and primary antibodies over the amount of antigen. Thus, the complex of antigen with the primary antibody was completely labeled with the secondary antibody and detected by laser-induced fluorescence. This important consideration has been demonstrated in all electropherograms, which always show the presence of peak 1 (excess unbound secondary antibody) and peak 2 (complex of primary and secondary antibodies). Peak 4, which is also present in all electropherograms, arises from the free fluorophore, tetramethylrhodamine, an impurity present in the secondary antibody reagent. We used peak 4 as an internal standard to correct for changes of instrument sensitivity. Because the primary antibody is saturated with the secondary antibody and because the fluorescence from the same secondary antibody is measured, the relative fluorescence intensity from one mole of Tg is equal to that from one mole of BrdU.

Thus, Tg was quantified from measured fluorescence intensities using calibration against BrdU-DNA standards.

Using the BrdU calibration, we determined that irradiation of A549 cells with 1 Gy yields 0.9±0.2 Tg per $10^7$ DNA bases. This agrees with a previous report [Cooper et al. (1997) Science 275:990] showing that irradiation of human fibroblasts with 10 Gy of X-rays produces 0.95±0.12 Tg per $10^6$ DNA bases. A typical series of electropherograms obtained with DNA extracted from irradiated human A549 lung carcinoma cells is shown in FIG. 4.

FIG. 4 shows representative electropherograms showing the yield of thymine glycol (Tg) in A549 human lung carcinoma cells irradiated with increasing doses (0.01 to 0.2 Gy) from a $^{137}$Cs γ-ray source. A sample of the extracted cellular DNA was incubated with the TMR-labeled secondary anti-mouse monoclonal antibody in 10 mM Tris-HCl (pH 7.3) for 5 min at room temperature (20–25 ° C.) and further incubated with a primary mouse monoclonal anti-Tg antibody under the same conditions for another 20 min. A 1-nl aliquot of the mixture containing 25 μg/ml of DNA was injected onto the capillary for the assay.

The signal with unirradiated DNA was so low that despite the use of a fairly protracted extraction protocol, it was possible to detect Tg at doses below 0.05 Gy. The Tg signal detected after 0.05 Gy irradiation corresponds to 4.3 Tg per $10^9$ bases. The extraction protocol involved culturing cells in Dulbecco's modified Eagle's medium/F12 medium supplemented with 10% fetal bovine serum. The medium was discarded immediately before irradiation and the cells were rinsed and then held in ice-cold phosphate buffered saline during irradiation. The cells were irradiated in a Shepherd Mark I-68A $^{137}$Cs Irradiator (J. L. Shepherd and Associates, San Fernando, Calif.). Radiation exposure to the desired dose was kept in all cases to less than 3 min. Immediately after irradiation (or a period of repair in medium at 37° C.), the cells were lysed by 30-min incubation at 60° C. in NET buffer [50 mM Tris-HCl (pH 9.0), 150 mM NaCl, 15 mM EDTA] containing 0.02% SDS and 20 mg/ml proteinase K. Nucleic acids were extracted and precipitated. RNA was removed, after resuspension of the samples in 1% NET buffer, by addition of RNase A (10 mg/ml) and RNase TI (10 units/ml) and incubation at 37° C. for 30 min. Nucleic acids were again extracted and precipitated and the DNA dissolved in 10 mM Tris-HCl (pH 7.6) and 1 mM EDTA. DNA concentrations were determined by UV spectrometry. The results show that the detection limit, based on a signal-to-noise ratio of three was ~1 Tg per $10^9$ bases.

B. Yield of Thymine Glycol In Irradiated Naked DNA Versus Cellular DNA

Figure 5A:
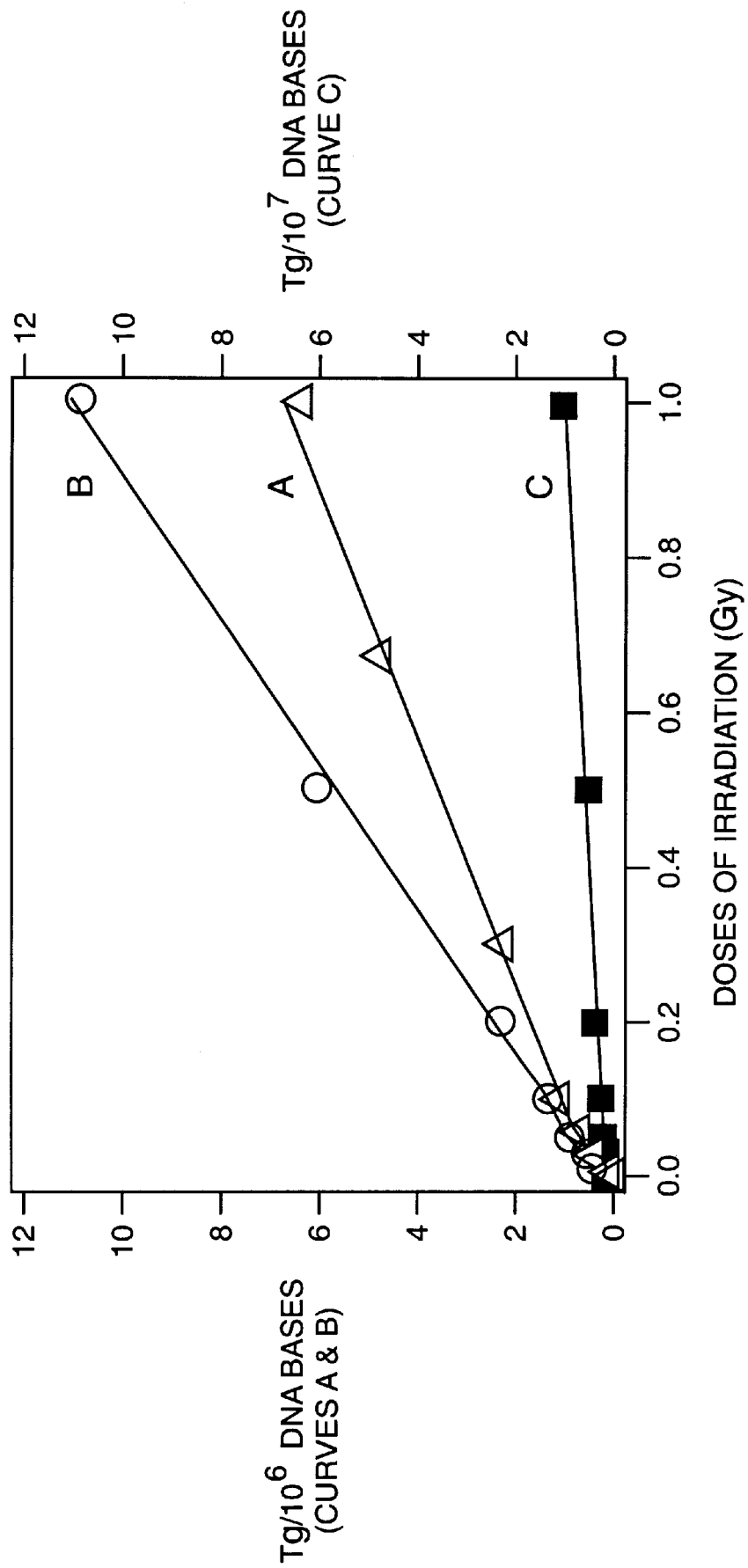
FIG. 5 shows a comparison of the yield of Tg generated by 0.01 to 1 Gy irradiation of calf thymus DNA (A), naked DNA extracted from A549 cells (B), and the A549 cells (C).
Figure 5B:
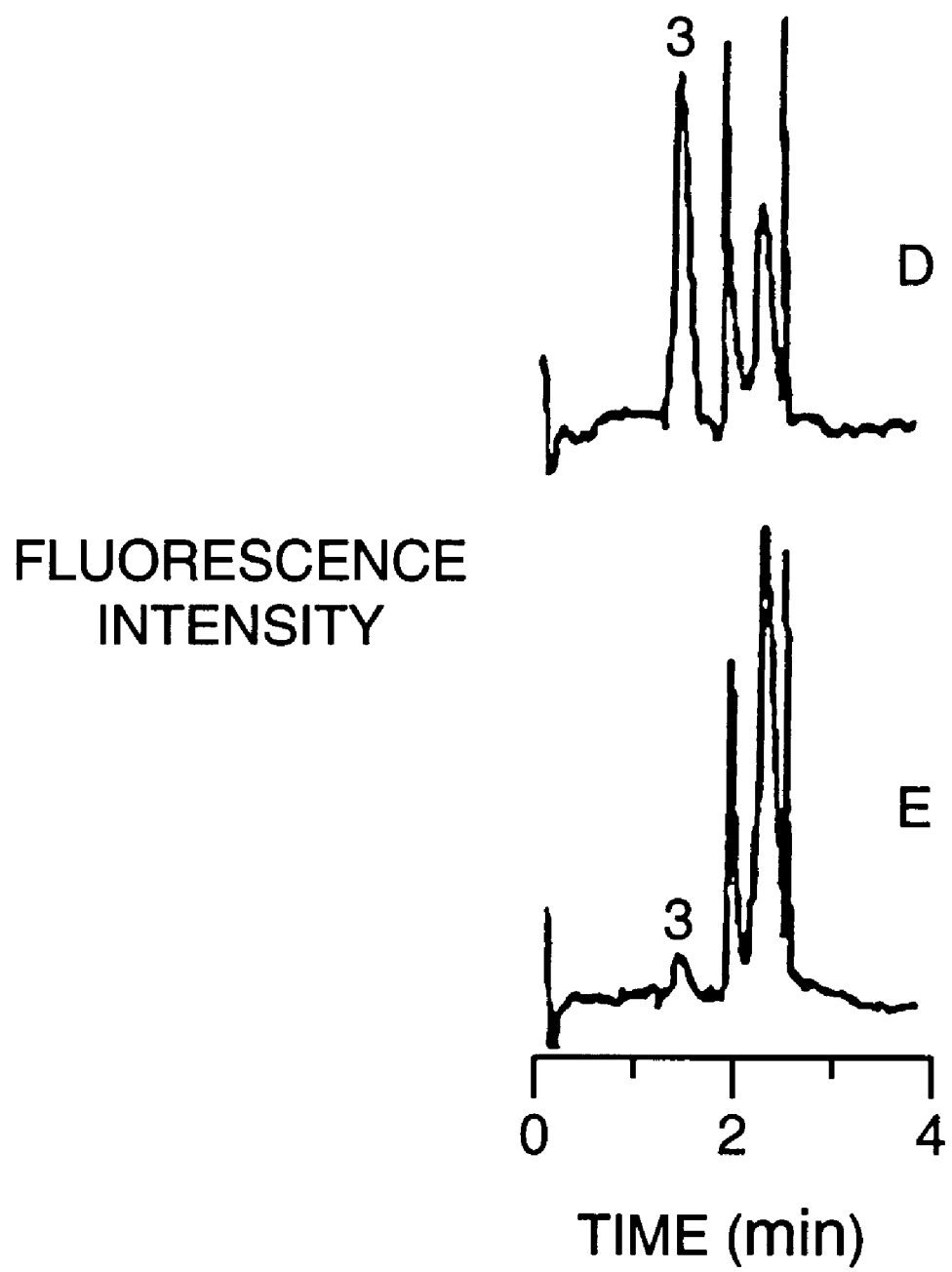

The dose response for the yield of Tg produced by up to 1 Gy irradiation was compared for naked DNA and cellular DNA. FIG. 5 shows the results of a comparison of the yield of Tg generated by 0.01 to 1 Gy irradiation of calf thymus DNA (A), naked DNA extracted from A549 cells (B), and the A549 cells (C). The left vertical axis is for curves A and B, and the right axis is for curve C. Calf thymus DNA in aqueous solution (Sigma) was directly irradiated with the specified doses and the Tg then assayed. A549 cells and the naked DNA extracted from A549 cells were separately irradiated with the specified doses and the Tg then assayed. The ratios of the slopes of the linear curves are 72 (A over C) and 122 (B over C), respectively, which represents the protection factor afforded by the cells to the DNA. Comparison of 5-Gy irradiated calf thymus DNA before (D) and after (E) the treatment with *Escherichia coli* endonuclease III (6 ng enzyme per 1 μg DNA) confirmed that peak 3 was due to Tg.

FIG. 5 shows that for naked DNA, either isolated from A549 cells or a preparation of commercially available calf thymus DNA, there was a linear response up to 1 Gy and thereafter saturation was observed unless the DNA was diluted or the amounts of secondary and primary antibody were increased. Linearity was observed with DNA from irradiated A549 cells up to and including 5 Gy, the highest dose examined. The slopes of the three curves indicate that 1 Gy induces 0.9 Tg per $10^7$ bases in cellular DNA, 11 Tg per $10^6$ bases in naked DNA extracted from A549 cells, and 6.5 Tg per $10^6$ bases in calf thymus DNA in dilute aqueous solution. Thus the cell affords ~70 to 120 fold protection to its DNA, consistent with previous data [Chaudhry and Weinfeld (1995) J. Mol. Biol. 249:914; Ljungman (1991) Radiat. Res. 126:58; Ljungman et al. (1991) Radiat. Res. 127:17115].

Confirmation that the assay was measuring Tg was obtained by incubation of 5 Gy irradiated DNA (FIG. 5D) with Escherichia coli endonuclease III, resulting in the almost complete loss of peak 3 (FIG. 5E).

C. Radiation Induced Repair Of Thymine Glycol In Human Lung Carcinoma Cells

This experiment was conducted in order to monitor removal of thymine glycol from cells irradiated with a typical clinical dose of ionizing radiation, and to determine whether the rate of removal was affected by a prior low dose exposure. Eukaryotic cells are known to have an inducible or adaptive response that enhances their radioresistance after a low priming dose of radiation [Olivieri et al. (1984) Science 223:594; Wolff et al. (1988) Int. J. Radiat. Biol. 53:39; Marples and Skov (1996) Radiat. Res. 146:382]. There is also evidence suggesting that a substantial component of radioresistance shown by tumor cells may be inducible rather than constitutive [Joiner et al. (1996) Mutat. Res. 358:171; Lambin et al. (1996) Int. J. Radiat. Biol. 69:279; Marples et al. (1997) Int. J. Radiat. Biol. 71:721]. Because hydrogen peroxide, another DNA damaging agent, similarly enhances resistance to subsequent X-irradiation [Marples and Joiner (1995) Radiat. Res. 141:160], and because the adaptive response appears to be inhibited by agents that inhibit DNA repair and protein synthesis [Marples et al. (1997) Int. J. Radiat. Biol. 71:721; Marples and Joiner (1995) Radiat. Res. 141:160; Youngblom et al. (1989) Mutat. Res. 227:257; Seong et al. (1995) Int. J. Radiat. Oncol. Biol. Phys. 33:869], enhanced DNA repair, especially that of double-strand breaks [Ikushima et al. (1996) Mutat. Res. 358:193; Lehnert and Chow (1997) Radiat. Environ. Biophys. 36:67], has been implicated as a mechanism underlying the inducible response. However, this phenomenon has not been examined directly by monitoring the repair of DNA base lesions.

Toward this end, we irradiated A549 cells with either a typical clinical dose of 2 Gy or with 0.25 Gy four hours before the 2-Gy irradiation. Removal of Tg was then monitored over a 24-hour period. The results are shown in FIG. 6.

Figure 6A:
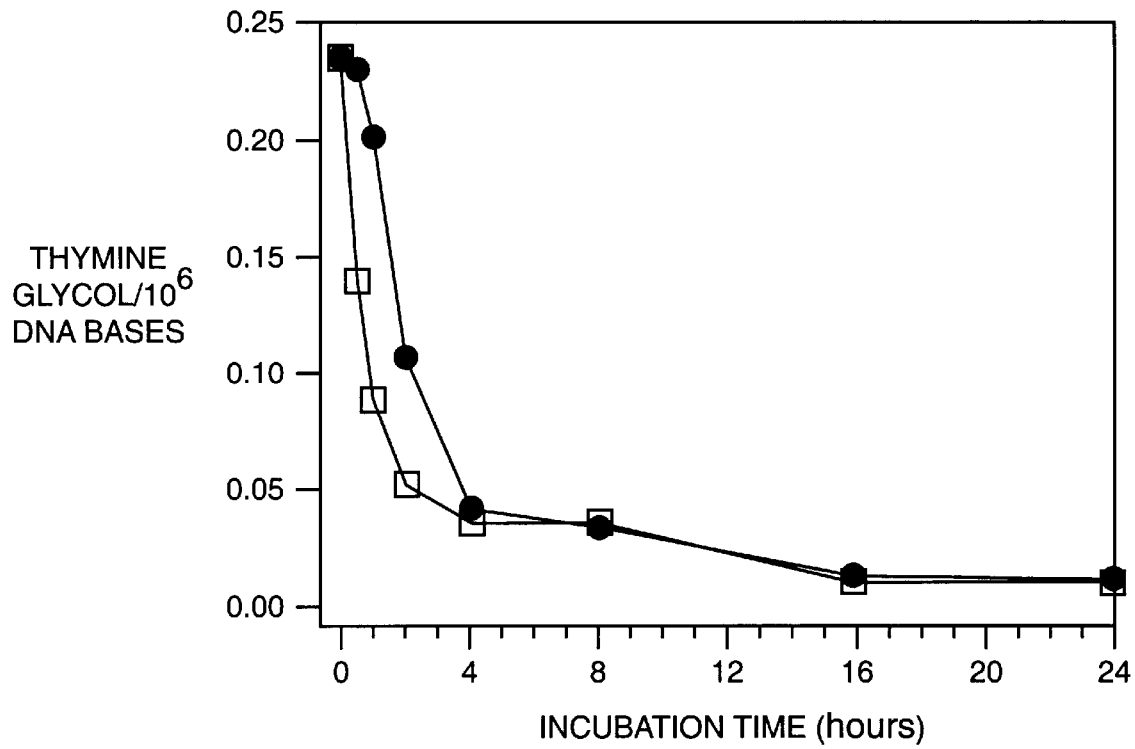
FIG. 6 shows a comparison of removal of Tg by A549 cells with and without a priming dose of radiation.
Figure 6B:
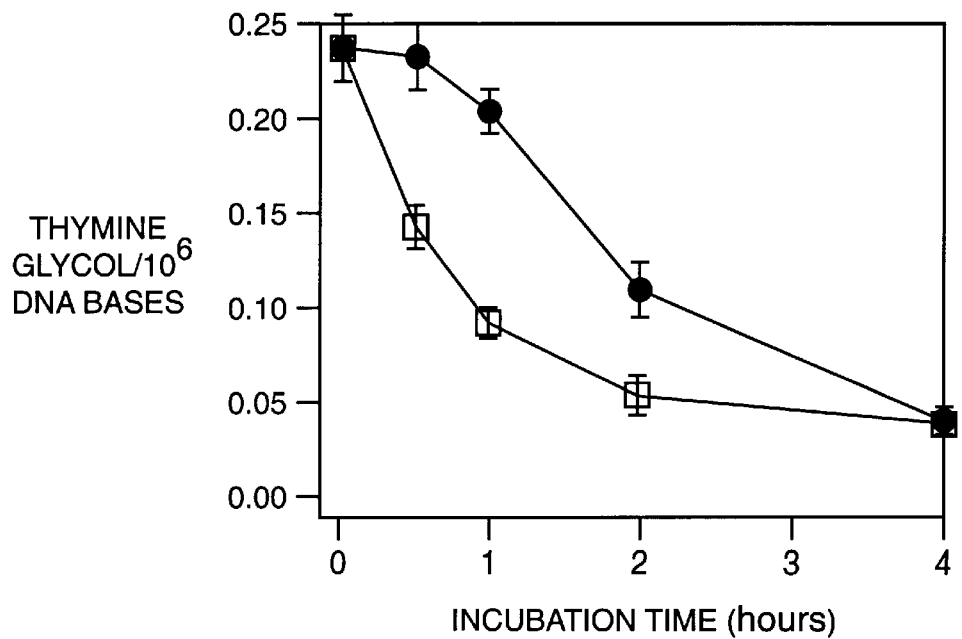

FIG. 6 shows a comparison of removal of Tg by A549 cells with and without a priming dose of radiation. A549 cells were irradiated with 2 Gy and then incubated at 37° C. for the specified time before the DNA was extracted (●), or given a priming dose of 0.25 Gy and incubated at 37° C. for four hours before the 2-Gy dose and then allowed to carry out repair (□). The insert shows an expanded region between 0 and 4 hours. The error bars represent one standard deviation from six replicate assays of duplicate sets of cells.

The results in FIG. 6 show that without prior low-dose irradiation there was a reasonably rapid removal of up to 80% of Tg over the first four hours (FIG. 6), although there was a perceptible lag in repair over the first 30 min. Prior low-dose irradiation did not alter the initial induction of Tg after the 2-Gy dose, but clearly enhanced the initial rate of lesion removal, reducing the time for 50% removal from ~100 min to ~50 min. Much of this appears attributable to the absence of an early lag period. Thus, our experiments suggest that there is an inducible repair response for radiation-induced DNA base damage.

EXAMPLE 3

Detection And Quantitation Of Mismatches And Mutations In DNA Using *Escherichia coli* MutS Protein In order to detect and quantitate mismatches in DNA, a sample containing the DNA which is suspected of containing mismatches is incubated with MutS protein under previously described conditions [Lirincy et al. (1988)]. In a first approach, a saturating amount of fluorescently labeled MutS protein is incubated with the DNA sample, coupled with separation of the resulting fluorescent molecular entities by capillary electrophoresis and laser-induced fluorescent as described supra. In a second approach, MutS protein is incubated with saturating amounts of fluorescently labeled anti-MutS antibody prior to incubation with the DNA sample and subsequent analysis using capillary electrophoresis and laser-induced fluorescence in order to quantitate nucleic acid mismatches.

In order to detect and quantitate mutations in DNA, a sample containing the DNA which is suspected of containing mutations is incubated with MutS protein under previously described conditions [Lishanski et al. (1994)]. Briefly, DNA containing a mutation of interest is amplified using PCR, and the PCR products are annealed to a wild-type DNA strand. The resulting double-stranded DNA is incubated either with a saturating amount of fluorescently labeled MutS protein, or with MutS protein previously incubated with saturating amounts of fluorescently labeled anti-MutS antibody. The resulting mixture is analyzed by capillary electrophoresis and laser-induced fluorescent as described supra in order to quantitate nucleic acid mutations.

EXAMPLE 4

Detection And Quantitation of Benzo[a]Pyrene Diol Epoxide Adducts in DNA

Benzo[a]pyrene (BaP) is an incomplete combustion product of fossil fuels from industrial processes as well as from charbroiled meat and cigarette smoke. Benzo[a]pyrene diol epoxide (BPDE), the electrophilic reactive metabolite of BaP, has long been known to be carcinogenic. It forms DNA adducts through electrophilic reaction with guanine. Because of the chronic environmental exposure to low levels of this carcinogen, there is a need for methods for quantitating low levels of BPDE adducts.

For the quantitation of trace levels of BPDE adducts, we use a similar approach as described in Example 2 for the quantitation of thymine glycol. Briefly, mouse monoclonal antibody specific for BPDE adducts [Booth et al. (1994) Carcinogenesis 15: 2099–2106] is used in combination with tetramethylrhodamine labeled anti-mouse IgG antibody (Calbiochem, San Diego, Calif.; Sigma, St. Louis, Mo.; and Cedarlane Laboratories Ltd., Homby, Ontario, Canada) to bind to BPDE adducts which are obtained by either treating calf thymus DNA with BPDE or treating animal cells with benzo[a]pyrene.

In order to determine the feasibility of this approach, mouse monoclonal antibody specific for BPDE adducts was incubated with tetramethylrhodamine labeled anti-mouse IgG antibody and the resulting mixture analyzed by capillary electrophoresis and laser-induced fluorescence. The results are shown in FIG. 10.

FIG. 10 shows electropherograms showing the separation of fluorescently labeled anti-mouse IgG antibody (peak 1) and the complex of mouse anti-benzo[a]pyrene diol epoxide (BPDE) antibody with fluorescently labeled anti-mouse IgG antibody (peak 2). The sample in FIG. 10(A) contained 1 pg (1 nl of 1 $\mu$g/ml solution) of tetramethylrhodamine (TMR) labeled anti-mouse secondary antibody (Calbiochem, La Jolla, Calif.) in 10 mM Tris-HCl buffer (pH 7.3); The sample in FIG. 10(B) contained a mixture of (A) and 0.25 pg of anti-BPDE adducts mouse monoclonal antibody. The sample in FIG. 10(C) contained a mixture of (A) and 0.5 pg of anti-BPDE mouse monoclonal antibody. The electropherograms were obtained by using a lab-built capillary electrophoresis system with laser-induced fluorescence detection. Separation was carried out in a 42 cm long, 20 $\mu$m inner diameter and 145 $\mu$m outer diameter fused silica capillary at an electric field of 400 V/cm. The detection window was 35 cm from the injection end of the capillary. The separation buffer (pH 12) contained 20 mM borate and 10 mM Tris-HCl. Electrokinetically injected sample volume was 1 nanoliter ($10^{-9}$ liter).

The results in FIG. 10 confirm our finding that a primary antibody which is specific for BPDE adducts in DNA and which is fluorescently labeled with a fluorescent secondary antibody may be used to quantitate BPDE adducts in DNA. In other words, where a sample containing BPDE adducts is used in the above-described method, peak 3 (which temporally appears before peak 1) is expected to be observed in the electropherogram as a result of the complexing of BPDE adducts with primary and secondary antibodies.

EXAMPLE 5

Detection And Quantitation Of DNA Base Damage Using UvrA and UvrB Proteins

UvrA and UvrB proteins are involved in DNA nucleotide excision repair processes. These proteins locate and identify base damage in the genome, a process referred to as damage-specific recognition. UvrA protein functions as a "molecular matchmaker" which delivers UvrB protein to sites of damage in DNA by the formation of a transient $(UvrA)_2(UvrB)_1$-DNA complex from which it rapidly dissociates, leaving a highly stable UvrB-DNA complex. We make use of the damage-specific recognition property of UvrA and UvrB proteins to bind to, and quantitate, a number of DNA base modifications including cyclobutane pyrimidine dimers, 6,4-photoproducts, benzo[a]pyrene adducts, dimethylbenzanthracene adducts, cis-platinum adducts, aflatoxin adducts, psoralen adducts, anthramycin adducts, mitomycin C adducts, N-acetoxy-2-aminofluorene adducts, and N-hydroxy-2-aminofluorene adducts.

UvrA and UvrB proteins are purified from *Escherichia coli* using previously described methods [Thomas et al. (1985) Journal of Biological Chemistry 260: 9875–9883].

Detection and quantitation of DNA damage to which the UvrA/UvrB complex binds is performed by either using fluorescently labeled anti-UvrB antibody in combination with UvrA, or fluorescently labeled UvrB as described below.

i. Using fluorescently labeled anti-UvrB antibody

To detect and quantify DNA base modifications, predetermined saturating amounts of fluorescently labeled anti-mouse IgG, UvrA and UvrB, and of mouse monoclonal antibody to UvrB [Kovalsky and Grossman (1994)], are mixed with a sample of interest which is suspected of containing DNA base modifications. An aliquot of the mixture is injected into the electrophoretic separation capillary to separate the five fluorescent molecular entities of interest, which include (i) unbound fluorescently labeled anti-mouse IgG, (ii) complex of fluorescently labeled anti-mouse IgG with mouse monoclonal anti-UvrB, (iii) complex of fluorescently labeled anti-mouse IgG, mouse monoclonal anti-UvrB, and UvrB, (iv) complex of fluorescently labeled anti-mouse IgG, mouse monoclonal anti-UvrB, UvrB, and UvrA, and (v) complex of fluorescently labeled anti-mouse IgG, mouse monoclonal anti-UvrB, UvrB, UvrA, and DNA base modification. Laser-induced fluorescence is used to measure the fluorescent intensity of each fluorescent molecular entity as described in Example 2. Calibration of fluorescent intensity against known amounts of DNA damage will give quantitative information on the levels of DNA damage present in the sample.

ii. Using fluorescently labeled UvrB protein

Alternatively, we can fluorescently label UvrB protein. UvrB protein (consisting of 673 amino acids) has a single cysteine residue (amino acid 303). The cysteine residue is reacted with a thiol-reactive fluorescent probe (e.g., those from Molecular Probes) under conditions recommended by the supplier. The fluorescently labeled UvrB will be used as an affinity probe for the assay of DNA base modifications as follows.

Pre-determined saturating amounts of UvrA and fluorescently labeled UvrB are mixed with a sample of interest which is suspected of containing the DNA base modification. An aliquot of the mixture is injected into the electrophoretic separation capillary in order to separate the three fluorescent molecular entities: (i) unbound fluorescently labeled UvrB, (ii) complex of UvrA and UvrB, and (iii) complex of UvrA, UvrB, and DNA base modification. Laser-induced fluorescence is used to measure the fluorescent intensity of each fluorescent molecular entity as separated in Example 2. Calibration of fluorescent intensity against known amounts of DNA damage will give quantitative information on the levels of DNA damage present in the sample.

EXAMPLE 6

Detection And Quantitation Of DNA Single-Strand And Double-Strand Breaks Using Poly(ADP-Ribose) Polymerase (PARP) And DNA-Dependent Protein Kinase (DNA-PK)

DNA strand breaks are common lesions generated by many carcinogens and antineoplastic agents, including ionizing radiation, alkylating agents (e.g., methylmethane sulfonate and 1,3-bis(2-chloroethyl)-1-nitrosourea) and enediynes (e.g., bleomycin). In general, single-strand breaks are far more common than double-strand breaks, but the latter are considered to be more deleterious because repair is more complicated and there is greater potential for loss of genetic information. Poly(ADP-ribose) polymerase (PARP) and DNA-dependent protein kinase (DNA-PK) are two enzyme known to strongly bind to strand breaks.

Detection and quantitation of single-strand and double-strand DNA breaks is performed by either using fluorescently labeled DNA-damage recognition proteins (PARP or DNA-PK), or fluorescently labeled antibody to the DNA-damage recognition proteins in combination with the unlabeled DNA-damage recognition proteins as described below.

i. Using fluorescently labeled anti-poly(ADP-ribose) polymerase antibody and anti-DNA-dependent protein kinase antibody To detect and quantify DNA strand breaks using the DNA binding domain of PARP, an unlabeled primary antibody which binds to the DNA binding domain of PARP is used in combination with a fluorescently labeled secondary antibody as follows. Pre-determined saturating amounts of fluorescently labeled anti-mouse IgG, PARP, and mouse monoclonal antibody to PARP are mixed with a sample of interest which is suspected of containing DNA strand breaks. An aliquot of the mixture is injected into the electrophoretic separation capillary to separate the four fluorescent molecular entities of interest, which include (i) unbound fluorescently labeled anti-mouse IgG, (ii) complex of fluorescently labeled anti-mouse IgG with mouse monoclonal anti-PARP, (iii) complex of fluorescently labeled anti-mouse IgG, mouse monoclonal anti-PARP, and PARP, (iv) complex of fluorescently labeled anti-mouse IgG, mouse monoclonal anti-PARP, and PARP and DNA with strand breaks. Laser-induced fluorescence is used to measure the fluorescent intensity of each fluorescent molecular entity as described in Example 2. Calibration of fluorescent intensity against known amounts of DNA damage will give quantitative information on the levels of DNA damage present in the sample. Standards are prepared by generating DNA-single strand breaks in plasmid DNA using a restriction enzyme in the presence of ethidium bromide [Weinfeld et al. (1997) Radiation Res. 148:22–28].

Alternatively, a fluorescently labeled primary antibody specific for the DNA-damage recognition protein is used in the absence of a secondary antibody as follows. Pre-determined saturating amounts of fluorescently labeled mouse monoclonal antibody to PARP are mixed with a sample of interest which is suspected of containing DNA strand breaks. An aliquot of the mixture is injected into the electrophoretic separation capillary to separate the fluorescent molecular entities of interest, which include (i) unbound fluorescently labeled anti-PARP, (ii) complex of fluorescently labeled anti-PARP antibody and PARP, and (iii) complex of fluorescently labeled anti-PARP antibody, PARP and DNA with strand breaks. Laser-induced fluorescence is used to measure the fluorescent intensity of each fluorescent molecular entity as described in Example 2. Calibration of fluorescent intensity against known amounts of DNA damage will give quantitative information on the levels of DNA damage present in the sample.

To detect and quantify DNA strand breaks using DNA-PK, the same steps described in the above two paragraphs are repeated with the exception that DNA-PK is substituted for PARP and appropriate corresponding antibodies are used. Standards for DNA double-strand breaks are prepared by digesting plasmid DNA with a restriction enzyme.

ii. Using fluorescently labeled poly(ADP-ribose) polymerase and DNA-dependent protein kinase Alternatively, we can also use fluorescently labeled poly (ADP-ribose) polymerase and fluorescently labeled DNA-dependent protein kinase as discussed above for UvrB. Briefly, pre-determined saturating amounts of fluorescently labeled poly(ADP-ribose) polymerase or fluorescently labeled DNA-dependent protein kinase are mixed with a sample of interest which is suspected of containing the DNA base modification. An aliquot of the mixture is injected into the electrophoretic separation capillary in order to separate the fluorescent molecular entities: (i) unbound fluorescently labeled DNA-damage recognition protein, and (ii) fluorescently labeled complex of the DNA-damage recognition protein bound to DNA strand breaks. Laser-induced fluorescence is used to measure the fluorescent intensity of each fluorescent molecular entity as separated in Example 2. Calibration of fluorescent intensity against known amounts of DNA damage will give quantitative information on the levels of DNA damage present in the sample.

From the above, it is clear that the present invention provides methods for detecting and measuring any modifications of interest in any nucleic acid sequence. The methods of the invention have the advantage of being sensitive, detecting zeptomole ($10^{-21}$ mole) levels of nucleic acid modifications, and are thus ten thousand to one hunderd thousand times more sensitive than prior art methods. In addition these methods are specific for the nucleic acid modification of interest, and require only nanogram amounts of nucleic acid sequence sample, as compared to microgram amounts of nucleic acid sequence sample which is required by prior art methods. Furthermore, the methods of the invention do not require the use of hazardous radioactive compounds. Importantly, the methods of the invention are also more accurate than prior art methods since they avoid potential artifacts which are caused by chemical or enzymatic digestion of nucleic acids. Moreover, the methods of the invention provide information more rapidly than prior art methods which require lengthy extensive enzymatic digestion and/or chemical derivatization of nucleic acid sequences.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and related fields are intended to be within the scope of the following claims.

What is claimed is:

1. A method for quantitating at least one modification of interest in a deoxyribonucleic nucleic acid sequence contained in a sample, comprising:
   a) providing:
      i) a sample suspected of containing a deoxyribonucleic nucleic acid sequence comprising said at least one modification of interest;
      ii) an antibody which specifically binds to said at least one modification of interest; and
      iii) a fluorescently labeled second polypeptide sequence which specifically binds to said antibody;
   b) combining said sample, said antibody and said fluorescently labeled second polypeptide sequence to produce a fluorescently labeled second polypeptide sequence:antibody:deoxyribonucleic nucleic acid sequence complex, and a fluorescently labeled second polypeptide sequence:antibody complex;
   c) separating said fluorescently labeled second polypeptide sequence:antibody:deoxyribonucleic nucleic acid sequence complex, said fluorescently labeled second polypeptide sequence:antibody complex and said fluorescently labeled second polypeptide sequence by capillary electrophoresis;
   d) detecting said separated fluorescently labeled second polypeptide sequence:antibody:deoxyribonucleic nucleic acid sequence complex by laser-induced fluorescence; and
   e) quantitating said separated second polypeptide sequence:antibody:deoxyribonucleic nucleic acid sequence complex, thereby quantitating said at least one modification of interest in said nucleic acid sequence.

2. The method of claim 1, wherein said at least one modification of interest is selected from the group consisting of mutation mismatch, DNA adduct, and strand break.

3. The method of claim 1, wherein said antibody is monoclonal.

4. The method of claim 1, wherein said fluorescently labeled second polypeptide sequence is a fluorescently labeled antibody.

5. The method of claim 2, wherein said mutation is selected from the group consisting of deletion, insertion and substitution.

6. The method of claim 2, wherein said strand break is selected from the group consisting of single-strand break and double-strand break.

7. The method of claim 4, wherein said fluorescently labeled antibody is monoclonal.

8. A method for quantitating at least one modification of interest in a deoxyribonucleic nucleic acid sequence contained in a sample, comprising:
   a) providing:
      i) a sample suspected of containing a deoxyribonucleic nucleic acid sequence comprising said at least one modification of interest;
      ii) UvrA which specifically binds to said at least one modification of interest; and
      iii) fluorescently labeled UvrB which specifically binds to said UvrA;
   b) combining said sample, said UvrA and said fluorescently labeled UvrB to produce a fluorescently labeled UvrB:UvrA:deoxyribonucleic nucleic acid sequence complex, and a fluorescently labeled UvrB:UvrA complex;
   c) separating said fluorescently labeled UvrB:UvrA:deoxyribonucleic nucleic acid sequence complex said fluorescently labeled UvrB:UvrA complex and said fluorescently labeled UvrB by capillary electrophoresis;
   d) detecting said separated fluorescently labeled UvrB:UvrA:deoxyribonucleic nucleic acid sequence complex by laser-induced fluorescence; and
   e) quantitating said separated UvrB:UvrA:deoxyribonucleic nucleic acid sequence complex, thereby quantitating said at least one modification of interest in said nucleic acid sequence.

9. A method for quantitating at least one modification of interest in a nucleic acid sequence contained in a sample, comprising:
   a) providing:
      i) a sample suspected of containing a nucleic acid sequence comprising said at least one modification of interest;
      ii) a UvrA:UvrB complex; and
      ii) a fluorescently labeled antibody which specifically binds to UvrB;
   b) combining said sample, said UvrA:UvrB complex and said fluorescently labeled antibody to produce a fluorescently labeled nucleic acid sequence:UvrA:UvrB:antibody complex;
   c) separating said fluorescently labeled nucleic acid sequence:UvrA:UvrB:antibody complex and said fluorescently labeled polypeptide sequence by capillary electrophoresis;
   d) detecting said separated fluorescently labeled nucleic acid sequence:UvrA:UvrB:antibody complex by laser-induced fluorescence; and
   e) quantitating said separated nucleic acid sequence:UvrA:UvrB:antibody complex, thereby quantitating said at least one modification of interest in said nucleic acid sequence.

10. A method for quantitating a mutation caused by at least one modification selected from the group consisting of deletion, insertion and substitution in a deoxyribonucleic nucleic acid sequence contained in a sample, comprising:
 a) providing:
  i) a sample suspected of containing a deoxyribonucleic nucleic acid sequence comprising at least one modification;
  ii) a first polypeptide sequence which specifically binds to said modification; and
  iii) a fluorescently labeled second polypeptide sequence which specifically binds to said first polypeptide sequence;
 b) combining said sample, said first polypeptide sequence and said fluorescently labeled second polypeptide sequence to produce a fluorescently labeled second polypeptide sequence first polypeptide sequence:deoxyribonucleic nucleic acid sequence complex, and a fluorescently labeled second polypeptide sequence:first polypeptide sequence complex;
 c) separating said fluorescently labeled second polypeptide sequence:first polypeptide sequence:deoxyribonucleic nucleic acid sequence complex, said fluorescently labeled second polypeptide sequence:first polypeptide sequence complex and said fluorescently labeled second polypeptide sequence by capillary electrophoresis;
 d) detecting said separated fluorescently labeled second polypeptide sequence:first polypeptide sequence:deoxyribonucleic nucleic acid sequence complex by laser-induced fluorescence; and
 e) quantitating said separated second polypeptide sequence:first polypeptide sequence:deoxyribonucleic nucleic acid sequence complex, thereby quantitating said mutation in said nucleic acid sequence.

11. The method of claim 10, wherein said first polypeptide sequence is an antibody.

12. The method of claim 10 wherein, said fluorescently labeled second polypeptide sequence is a fluorescently labeled antibody.

13. The method of claim 10, wherein said first polypeptide sequence is UvrA, and said second fluorescently labeled second polypeptide sequence is fluorescently labeled UvrB.

14. The method of claim 10, wherein said first polypeptide sequence is a UvrA:UvrB complex, and said fluorescently labeled second polypeptide sequence is a fluorescently labeled antibody which specifically binds to UvrB.

15. The method of claim 10, wherein said combining comprises mixing said sample with said fluorescently labeled second polypeptide sequence to produce a first mixture, followed by mixing said mixture with said first polypeptide sequence to produce a second mixture.

16. The method of claim 11 wherein, said antibody is monoclonal.

17. The method of claim 12, wherein said fluorescently labeled antibody is monoclonal.

18. The method of claim 14, wherein said fluorescently labeled antibody which specifically binds to UvrB is monoclonal.

19. A method for quantitating a mutation caused by a strand break in a deoxyribonucleic nucleic acid sequence contained in a sample, comprising:
 a) providing:
  i) a sample suspected of containing a deoxyribonucleic nucleic acid sequence comprising at least one mutation caused by a strand break;
  ii) a first polypeptide sequence which specifically binds to said mutation; and
  iii) a fluorescently labeled second polypeptide sequence which specifically binds to said first polypeptide sequence;
 b) combining said sample, said first polypeptide sequence and said fluorescently labeled second polypeptide sequence to produce a fluorescently labeled second polypeptide sequence:first polypeptide sequence:deoxyribonucleic nucleic acid sequence complex, and a fluorescently labeled second polypeptide sequence:first polypeptide sequence complex;
 c) separating said fluorescently labeled second polypeptide sequence:first polypeptide sequence:deoxyribonucleic nucleic acid sequence complex, said fluorescently labeled second polypeptide sequence:first polypeptide sequence complex and said fluorescently labeled second polypeptide sequence by capillary electrophoresis;
 d) detecting said separated fluorescently labeled second polypeptide sequence:first polypeptide sequence:deoxyribonucleic nucleic acid sequence complex by laser-induced fluorescence; and
 e) quantitating said separated second polypeptide sequence:first polypeptide sequence:deoxyribonucleic nucleic acid sequence complex, thereby quantitating said mutation in said nucleic acid sequence.

20. The method of claim 19, wherein said strand break is selected from the group consisting of single-strand breaks and double-strand breaks.

21. The method of claim 19 wherein, said first polypeptide sequence is poly(ADP-ribose) polymerase.

22. The method of claim 20, wherein said strand break is a double-strand break and said first polypeptide sequence is DNA-dependent protein kinase.

23. The method of claim 21, wherein said fluorescently labeled second polypeptide sequence is a fluorescently labeled antibody which specifically binds to said poly(ADP-ribose) polymerase.

24. The method of claim 22, wherein said fluorescently labeled second polypeptide sequence is a fluorescently labeled antibody which specifically binds to said DNA-dependent protein kinase.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 940 amino acids
      (B) TYPE: amino acid
      (C) STRANDEDNESS: Not Relevant
      (D) TOPOLOGY: unknown (ii) MOLECULE TYPE: protein (xi) SEQUENCE DESCRIPTION: SEQ ID NO:1:

```
Met Asp Lys Ile Glu Val Arg Gly Ala Arg Thr His Asn Leu Lys Asn
1               5                   10                  15

Ile Asn Leu Val Ile Pro Arg Asp Lys Leu Ile Val Val Thr Gly Leu
            20                  25                  30

Ser Gly Ser Gly Lys Ser Ser Leu Ala Phe Asp Thr Leu Tyr Ala Glu
            35                  40                  45

Gly Gln Arg Arg Tyr Val Glu Ser Leu Ser Ala Tyr Ala Arg Gln Phe
        50                  55                  60

Leu Ser Leu Met Glu Lys Pro Asp Val Asp His Ile Glu Gly Leu Ser
65                  70                  75                  80

Pro Ala Ile Ser Ile Glu Gln Lys Ser Thr Ser His Asn Pro Arg Ser
                85                  90                  95

Thr Val Gly Thr Ile Thr Glu Ile His Asp Tyr Leu Arg Leu Leu Phe
                100                 105                 110

Ala Arg Val Gly Glu Pro Arg Cys Pro Asp His Asp Val Pro Leu Ala
            115                 120                 125

Ala Gln Thr Val Ser Gln Met Val Asp Asn Val Leu Ser Gln Pro Glu
        130                 135                 140

Gly Lys Arg Leu Met Leu Leu Ala Pro Ile Ile Lys Glu Arg Lys Gly
145                 150                 155                 160

Glu His Thr Lys Thr Leu Glu Asn Leu Ala Ser Gln Gly Tyr Ile Arg
                165                 170                 175
```

```
Ala Arg Ile Asp Gly Glu Val Cys Asp Leu Ser Asp Pro Pro Lys Leu
            180                 185                 190

Glu Leu Gln Lys Lys His Thr Ile Glu Val Val Asp Arg Phe Lys
        195                 200                 205

Val Arg Asp Asp Leu Thr Gln Arg Leu Ala Glu Ser Phe Glu Thr Ala
    210                 215                 220

Leu Glu Leu Ser Gly Gly Thr Ala Val Val Ala Asp Met Asp Asp Pro
225                 230                 235                 240

Lys Ala Glu Glu Leu Leu Phe Ser Ala Asn Phe Ala Cys Pro Ile Cys
                245                 250                 255

Gly Tyr Ser Met Arg Glu Leu Glu Pro Arg Leu Phe Ser Phe Asn Asn
                260                 265                 270

Pro Ala Gly Ala Cys Pro Thr Cys Asp Gly Leu Gly Val Gln Gln Tyr
            275                 280                 285

Phe Asp Pro Asp Arg Val Ile Gln Asn Pro Glu Leu Ser Leu Ala Gly
        290                 295                 300

Gly Ala Ile Arg Gly Trp Asp Arg Arg Asn Phe Tyr Tyr Phe Gln Met
305                 310                 315                 320

Leu Lys Ser Leu Ala Asp His Tyr Lys Phe Asp Val Glu Ala Pro Trp
                325                 330                 335

Gly Ser Leu Ser Ala Asn Val His Lys Val Val Leu Tyr Gly Ser Gly
            340                 345                 350

Lys Glu Asn Ile Glu Phe Lys Tyr Met Asn Asp Arg Gly Asp Thr Ser
        355                 360                 365

Ile Arg Arg His Pro Phe Glu Gly Val Leu His Asn Met Glu Arg Arg
370                 375                 380

Tyr Lys Glu Thr Glu Ser Ser Ala Val Arg Glu Glu Leu Ala Lys Phe
385                 390                 395                 400

Ile Ser Asn Arg Pro Cys Ala Ser Cys Glu Gly Thr Arg Leu Arg Arg
                405                 410                 415

Glu Ala Arg His Val Tyr Val Glu Asn Thr Pro Leu Pro Ala Ile Ser
                420                 425                 430

Asp Met Ser Ile Gly His Ala Met Glu Phe Phe Asn Asn Leu Lys Leu
            435                 440                 445

Ala Gly Gln Arg Ala Lys Ile Ala Glu Lys Ile Leu Lys Glu Ile Gly
            450                 455                 460

Asp Arg Leu Lys Phe Leu Val Asn Val Gly Leu Asn Tyr Leu Thr Leu
465                 470                 475                 480

Ser Arg Ser Ala Glu Thr Leu Ser Gly Gly Glu Ala Gln Arg Ile Arg
                485                 490                 495

Leu Ala Ser Gln Ile Gly Ala Gly Leu Val Gly Val Met Tyr Val Leu
                500                 505                 510

Asp Glu Pro Ser Ile Gly Leu His Gln Arg Asp Asn Glu Arg Leu Leu
            515                 520                 525

Gly Thr Leu Ile His Leu Arg Asp Leu Gly Asn Thr Val Ile Val Val
530                 535                 540

Glu His Asp Glu Asp Ala Ile Arg Ala Ala Asp His Val Ile Asp Ile
545                 550                 555                 560

Gly Pro Gly Ala Gly Val His Gly Gly Glu Val Val Ala Glu Gly Pro
                565                 570                 575

Leu Glu Ala Ile Met Ala Val Pro Glu Ser Leu Thr Gly Gln Tyr Met
                580                 585                 590

Ser Gly Lys Arg Lys Ile Glu Val Pro Lys Lys Arg Val Pro Ala Asn
```

-continued

```
            595                 600                 605
Pro Glu Lys Val Leu Lys Leu Thr Gly Ala Arg Gly Asn Asn Leu Lys
    610                 615                 620

Asp Val Thr Leu Thr Leu Pro Val Gly Leu Phe Thr Cys Ile Thr Gly
625                 630                 635                 640

Val Ser Gly Ser Gly Lys Ser Thr Leu Ile Asn Asp Thr Leu Phe Pro
                645                 650                 655

Ile Ala Gln Arg Gln Leu Asn Gly Ala Thr Ile Ala Glu Pro Ala Pro
            660                 665                 670

Tyr Arg Asp Ile Gln Gly Leu Glu His Phe Asp Lys Val Ile Asp Ile
        675                 680                 685

Asp Gln Ser Pro Ile Gly Arg Thr Pro Arg Ser Asn Pro Ala Thr Tyr
    690                 695                 700

Thr Gly Val Phe Thr Pro Val Arg Glu Leu Phe Ala Gly Val Pro Glu
705                 710                 715                 720

Ser Arg Ala Arg Gly Tyr Thr Pro Gly Arg Phe Ser Phe Asn Val Arg
                725                 730                 735

Gly Gly Arg Cys Glu Ala Cys Gln Gly Asp Gly Val Ile Lys Val Glu
            740                 745                 750

Met His Phe Leu Pro Asp Ile Tyr Val Pro Cys Asp Gln Cys Lys Gly
        755                 760                 765

Lys Arg Tyr Asn Arg Glu Thr Leu Glu Ile Lys Tyr Lys Gly Lys Thr
770                 775                 780

Ile His Glu Val Leu Asp Met Thr Ile Glu Glu Ala Arg Glu Phe Phe
                790                 795                 800
785

Asp Ala Val Pro Ala Leu Ala Arg Lys Leu Gln Thr Leu Met Asp Val
            805                 810                 815

Gly Leu Thr Tyr Ile Arg Leu Gly Gln Ser Ala Thr Thr Leu Ser Gly
        820                 825                 830

Gly Glu Ala Gln Arg Val Lys Leu Ala Arg Glu Leu Ser Lys Arg Gly
    835                 840                 845

Thr Gly Gln Thr Leu Tyr Ile Leu Asp Glu Pro Thr Thr Gly Leu His
850                 855                 860

Phe Ala Asp Ile Gln Gln Leu Leu Asp Val Leu His Lys Leu Arg Asp
865                 870                 875                 880

Gln Gly Asn Thr Ile Val Val Ile Glu His Asn Leu Asp Val Ile Lys
                885                 890                 895

Thr Ala Asp Trp Ile Val Asp Leu Gly Pro Glu Gly Gly Ser Gly Gly
            900                 905                 910

Gly Glu Ile Leu Val Ser Gly Thr Pro Glu Thr Val Ala Glu Cys Glu
        915                 920                 925

Ala Ser His Thr Ala Arg Phe Leu Lys Pro Met Leu
    930                 935                 940
```

(2) INFORMATION FOR SEQ ID NO:2:

(i) SEQUENCE CHARACTERISTICS:
        (A) LENGTH: 673 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:2:

Met Ser Lys Pro Phe Lys Leu Asn Ser Ala Phe Lys Pro Ser Gly Asp

```
1               5                   10                  15
Gln Pro Glu Ala Ile Arg Arg Leu Glu Glu Gly Leu Glu Asp Gly Leu
                    20                  25                  30
Ala His Gln Thr Leu Leu Gly Val Thr Gly Ser Gly Lys Thr Phe Thr
                35                  40                  45
Ile Ala Asn Val Ile Ala Asp Leu Gln Arg Pro Thr Met Val Leu Ala
            50                  55                  60
Pro Asn Lys Thr Leu Ala Ala Gln Leu Tyr Gly Glu Met Lys Glu Phe
65                  70                  75                  80
Phe Pro Glu Asn Ala Val Glu Tyr Phe Val Ser Tyr Asp Tyr Tyr
                    85                  90                  95
Gln Pro Glu Ala Tyr Val Pro Ser Ser Asp Thr Phe Ile Glu Lys Asp
                100                 105                 110
Ala Ser Val Asn Glu His Ile Glu Gln Met Arg Leu Ser Ala Thr Lys
                115                 120                 125
Ala Met Leu Glu Arg Arg Asp Val Val Val Ala Ser Val Ser Ala
                130                 135                 140
Ile Tyr Gly Leu Gly Asp Pro Asp Leu Tyr Leu Lys Met Met Leu His
145                 150                 155                 160
Leu Thr Val Gly Met Ile Ile Asp Gln Arg Ala Ile Leu Arg Arg Leu
                165                 170                 175
Ala Glu Leu Gln Tyr Ala Arg Asn Asp Gln Ala Phe Gln Arg Gly Thr
                180                 185                 190
Phe Arg Val Arg Gly Glu Val Ile Asp Ile Phe Pro Ala Glu Ser Asp
            195                 200                 205
Asp Ile Ala Leu Arg Val Glu Leu Phe Asp Glu Glu Val Glu Arg Leu
            210                 215                 220
Ser Leu Phe Asp Pro Leu Thr Gly Gln Ile Val Ser Thr Ile Pro Arg
225                 230                 235                 240
Phe Thr Ile Tyr Pro Lys Thr His Tyr Val Thr Pro Arg Glu Arg Ile
                245                 250                 255
Val Gln Ala Met Glu Glu Ile Lys Glu Leu Ala Ala Arg Arg Lys
                260                 265                 270
Val Leu Leu Glu Asn Asn Lys Leu Leu Glu Glu Gln Arg Leu Thr Gln
                275                 280                 285
Arg Thr Gln Phe Asp Leu Glu Met Met Asn Glu Leu Gly Tyr Cys Ser
290                 295                 300
Gly Ile Glu Asn Tyr Ser Arg Phe Leu Ser Gly Arg Gly Pro Gly Glu
305                 310                 315                 320
Pro Pro Pro Thr Leu Phe Asp Tyr Leu Pro Ala Asp Gly Leu Leu Val
                325                 330                 335
Val Asp Glu Ser His Val Thr Ile Pro Gln Ile Gly Gly Met Tyr Arg
                340                 345                 350
Gly Asp Arg Ala Arg Lys Glu Thr Leu Val Glu Tyr Gly Phe Arg Leu
                355                 360                 365
Pro Ser Ala Leu Asp Asn Arg Pro Leu Lys Phe Glu Glu Phe Glu Ala
            370                 375                 380
Leu Ala Pro Gln Thr Ile Tyr Val Ser Ala Thr Pro Gly Asn Tyr Glu
385                 390                 395                 400
Leu Glu Lys Ser Gly Gly Asp Val Val Asp Gln Val Val Arg Pro Thr
                405                 410                 415
Gly Leu Leu Asp Pro Ile Ile Glu Val Arg Pro Val Ala Thr Gln Val
                420                 425                 430
```

```
Asp Asp Leu Leu Ser Glu Ile Arg Gln Arg Ala Ala Ile Asn Glu Arg
            435                 440                 445

Val Leu Val Thr Thr Leu Thr Lys Arg Met Ala Glu Asp Leu Thr Glu
    450                 455                 460

Tyr Leu Glu Glu His Gly Glu Arg Val Arg Tyr Leu Arg Ser Asp Ile
465                 470                 475                 480

Asp Thr Val Glu Arg Met Glu Ile Ile Arg Asp Leu Arg Leu Gly Glu
                485                 490                 495

Phe Asp Val Leu Val Gly Ile Asn Leu Leu Arg Glu Gly Leu Asp Met
                500                 505                 510

Pro Glu Val Ser Leu Val Ala Ile Leu Asp Ala Asp Lys Glu Gly Phe
                515                 520                 525

Leu Arg Ser Glu Arg Ser Leu Ile Gln Thr Ile Gly Arg Ala Ala Arg
    530                 535                 540

Asn Val Asn Gly Lys Ala Ile Leu Tyr Gly Asp Lys Ile Thr Pro Ser
545                 550                 555                 560

Met Ala Lys Ala Ile Gly Glu Thr Glu Arg Arg Arg Glu Lys Gln Gln
                565                 570                 575

Lys Tyr Asn Glu Glu His Gly Ile Thr Pro Gln Gly Leu Asn Lys Lys
                580                 585                 590

Val Val Asp Ile Leu Ala Leu Gly Gln Asn Ile Ala Lys Thr Lys Ala
            595                 600                 605

Lys Gly Arg Gly Lys Ser Arg Pro Ile Val Glu Pro Asp Asn Val Pro
            610                 615                 620

Met Asp Met Ser Pro Lys Ala Leu Gln Gln Lys Ile His Glu Leu Glu
625                 630                 635                 640

Gly Leu Met Met Gln His Ala Gln Asn Leu Glu Phe Glu Glu Ala Ala
                645                 650                 655

Gln Ile Arg Asp Gln Leu His Gln Leu Arg Glu Leu Phe Ile Ala Ala
            660                 665                 670

Ser
```

(2) INFORMATION FOR SEQ ID NO:3:

(i) SEQUENCE CHARACTERISTICS:
        (A) LENGTH: 1014 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:3:

```
Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
                20                  25                  30

Leu Arg Met Ala Ile Met Val Gln Ser Pro Met Phe Asp Gly Lys Val
            35                  40                  45

Pro His Trp Tyr His Phe Ser Cys Phe Trp Lys Val Gly His Ser Ile
            50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95
```

-continued

```
Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
            115                 120                 125

Met Glu Lys Ile Glu Lys Gly Gln Val Arg Leu Ser Lys Lys Met Val
            130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                    165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
            195                 200                 205

Lys Gly Asp Glu Val Asp Gly Val Asp Glu Val Ala Lys Lys Lys Ser
210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
            275                 280                 285

Phe Gly Ala Leu Leu Pro Cys Glu Glu Cys Ser Gly Gln Leu Val Phe
            290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
                340                 345                 350

Gln Asp Arg Ile Phe Pro Pro Glu Thr Ser Ala Ser Val Ala Ala Thr
            355                 360                 365

Pro Pro Pro Ser Thr Ala Ser Ala Pro Ala Ala Val Asn Ser Ser Ala
            370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
            435                 440                 445

Ala Asn Ile Arg Val Val Ser Glu Asp Phe Leu Gln Asp Val Ser Ala
            450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
```

-continued

```
            515                 520                 525
Gly Gly Ala Ala Val Asp Pro Asp Ser Gly Leu Glu His Ser Ala His
            530                 535                 540
Val Leu Glu Lys Gly Gly Lys Val Phe Ser Ala Thr Leu Gly Leu Val
545                 550                 555                 560
Asp Ile Val Lys Gly Thr Asn Ser Tyr Tyr Lys Leu Gln Leu Leu Glu
                565                 570                 575
Asp Asp Lys Glu Asn Arg Tyr Trp Ile Phe Arg Ser Trp Gly Arg Val
                580                 585                 590
Gly Thr Val Ile Gly Ser Asn Lys Leu Glu Gln Met Pro Ser Lys Glu
                595                 600                 605
Asp Ala Ile Glu Gln Phe Met Lys Leu Tyr Glu Lys Thr Gly Asn
            610                 615                 620
Ala Trp His Ser Lys Asn Phe Thr Lys Tyr Pro Lys Lys Phe Tyr Pro
625                 630                 635                 640
Leu Glu Ile Asp Tyr Gly Gln Asp Glu Glu Ala Val Lys Lys Leu Thr
                645                 650                 655
Val Asn Pro Gly Thr Lys Ser Lys Leu Pro Lys Pro Val Gln Asp Leu
                660                 665                 670
Ile Lys Met Ile Phe Asp Val Glu Ser Met Lys Lys Ala Met Val Glu
                675                 680                 685
Tyr Glu Ile Asp Leu Gln Lys Met Pro Leu Gly Lys Leu Ser Lys Arg
            690                 695                 700
Gln Ile Gln Ala Ala Tyr Ser Ile Leu Ser Glu Val Gln Gln Ala Val
705                 710                 715                 720
Ser Gln Gly Ser Ser Asp Ser Gln Ile Leu Asp Leu Ser Asn Arg Phe
                725                 730                 735
Tyr Thr Leu Ile Pro His Asp Phe Gly Met Lys Lys Pro Pro Leu Leu
            740                 745                 750
Asn Asn Ala Asp Ser Val Gln Ala Lys Val Glu Met Leu Asp Asn Leu
            755                 760                 765
Leu Asp Ile Glu Val Ala Tyr Ser Leu Leu Arg Gly Gly Ser Asp Asp
            770                 775                 780
Ser Ser Lys Asp Pro Ile Asp Val Asn Tyr Glu Lys Leu Lys Thr Asp
785                 790                 795                 800
Ile Lys Val Val Asp Arg Asp Ser Glu Glu Ala Glu Ile Ile Arg Lys
                805                 810                 815
Tyr Val Lys Asn Thr His Ala Thr Thr His Ser Ala Tyr Asp Leu Glu
            820                 825                 830
Val Ile Asp Ile Phe Lys Ile Glu Arg Glu Gly Glu Cys Gln Arg Tyr
            835                 840                 845
Lys Pro Phe Lys Gln Leu His Asn Arg Arg Leu Leu Trp His Gly Ser
850                 855                 860
Arg Thr Thr Asn Phe Ala Gly Ile Leu Ser Gln Gly Leu Arg Ile Ala
865                 870                 875                 880
Pro Pro Glu Ala Pro Val Thr Gly Tyr Met Phe Gly Lys Gly Ile Tyr
                885                 890                 895
Phe Ala Asp Met Val Ser Lys Ser Ala Asn Tyr Tyr His Thr Ser Gln
                900                 905                 910
Gly Asp Pro Ile Gly Leu Ile Leu Leu Gly Glu Val Ala Leu Gly Asn
            915                 920                 925
Met Tyr Glu Leu Lys His Ala Ser His Ile Ser Arg Leu Pro Lys Gly
            930                 935                 940
```

```
Lys His Ser Val Lys Gly Leu Gly Lys Thr Thr Pro Asp Pro Ser Ala
945             950             955             960

Asn Ile Ser Leu Asp Gly Val Asp Val Pro Leu Gly Thr Gly Ile Ser
            965             970                     975

Ser Gly Val Ile Asp Thr Ser Leu Leu Tyr Asn Glu Tyr Ile Val Tyr
                980             985             990

Asp Ile Ala Gln Val Asn Leu Lys Tyr Leu Leu Lys Leu Lys Phe Asn
            995             1000            1005

Phe Lys Thr Ser Leu Trp
    1010
```